United States Patent
Ebata

(10) Patent No.: US 11,607,202 B2
(45) Date of Patent: *Mar. 21, 2023

(54) ULTRASOUND DIAGNOSTIC APPARATUS, METHOD FOR CONTROLLING ULTRASOUND DIAGNOSTIC APPARATUS, AND READABLE RECORDING MEDIUM RECORDING A PROGRAM FOR CONTROLLING ULTRASOUND DIAGNOSTIC APPARATUS

(71) Applicant: FUJIFILM Corporation, Tokyo (JP)

(72) Inventor: Tetsurou Ebata, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/855,127

(22) Filed: Jun. 30, 2022

(65) Prior Publication Data

US 2022/0330923 A1 Oct. 20, 2022

Related U.S. Application Data

(60) Division of application No. 16/527,926, filed on Jul. 31, 2019, now Pat. No. 11,504,096, which is a
(Continued)

(30) Foreign Application Priority Data

Feb. 1, 2017 (JP) .............................. JP2017-016578

(51) Int. Cl.
*A61B 8/00* (2006.01)
*A61B 8/08* (2006.01)
(Continued)

(52) U.S. Cl.
CPC ............ *A61B 8/585* (2013.01); *A61B 8/5207* (2013.01); *A61B 8/5292* (2013.01); *A61B 8/54* (2013.01);
(Continued)

(58) Field of Classification Search
CPC ....... A61B 8/54; A61B 8/5207; A61B 8/5292; G06K 2209/05
See application file for complete search history.

(56) References Cited

U.S. PATENT DOCUMENTS 10,127,654 B2 11/2018 Murphy et al.
2006/0050960 A1 3/2006 Tu et al.
(Continued)

FOREIGN PATENT DOCUMENTS

| JP | 4-224738 A | 8/1992 |
| JP | 2002-253539 A | 9/2002 |
| JP | 2008-259622 A | 10/2008 |

OTHER PUBLICATIONS

Extended European Search Report for corresponding European Application No. 18747372.3, dated Jan. 3, 2020.
(Continued)

*Primary Examiner* — Ashley K Buran
*Assistant Examiner* — Sean V Blinder
(74) *Attorney, Agent, or Firm* — Birch, Stewart, Kolasch & Birch, LLP

(57) ABSTRACT

An ultrasound diagnostic apparatus 1 includes an image acquisition unit 3 that generates an ultrasound image, an image recognition unit 9 that performs image recognition for the ultrasound image to calculate recognition scores, an index value calculation unit 10 that calculates index values of a plurality of parts on the basis of the recognition scores calculated for a predetermined number of ultrasound images, a part narrowing-down unit 11 that narrows down
(Continued)

target parts for which part determination is to be performed, from the plurality of parts on the basis of the index values, and a part determination unit 12 that determines an imaging part of the subject on the basis of the recognition scores calculated by the image recognition unit 9 for the target parts narrowed down by the part narrowing-down unit 11.

25 Claims, 10 Drawing Sheets

Related U.S. Application Data continuation of application No. PCT/JP2018/001347, filed on Jan. 18, 2018.

(51) Int. Cl.
    *G06T 7/00* (2017.01)
    *G16H 50/70* (2018.01)
    *G06V 10/98* (2022.01)

(52) U.S. Cl.
    CPC .......... *G06T 7/0012* (2013.01); *G06T 7/0016* (2013.01); *G06V 10/98* (2022.01); *G06V 10/993* (2022.01); *G16H 50/70* (2018.01); *G06T 2207/10132* (2013.01)

(56) References Cited

U.S. PATENT DOCUMENTS

| | | |
|---|---|---|
| 2006/0269130 A1 | 11/2006 | Maroy et al. |
| 2007/0055153 A1 | 3/2007 | Simopoulos et al. |
| 2008/0025363 A1 | 10/2008 | Oosawa |
| 2016/0148373 A1 | 5/2016 | Robinson et al. |
| 2016/0174902 A1 | 6/2016 | Georgescu et al. |
| 2017/0143312 A1 | 5/2017 | Hedlund et al. |

OTHER PUBLICATIONS

International Preliminary Report on Patentability and Written Opinion of the International Searching Authority (Forms PCT/IB/326, PCT/IB/373 and PCT/ISA/237), dated Aug. 15. 2019, for International Application No. PCT/JP2018/001347, with an English Translation of the Written Opinion.

International Search Report, dated Mar. 6, 2018, for International Application No. PCT/JP2018/001347, with an English translation.

Japanese Office Action dated Apr. 14, 2020, for corresponding Japanese Patent Application No. 2018-566047, with an English translation.

Lee et al., "Identifying Multiple Abdominal Organs From CT Image Series Using a Multimodule Contextual Neural Network and Spatial Fuzzy Rules," IEEE Transactions on Information Technology in Biomedicine, vol. 7, No. 3, Sep. 2003, pp. 208-217.

U.S. Office Action for U.S. Appl. No. 16/527,926, dated Mar. 18, 2022 (Non-Final Rejection).

U.S. Office Action for U.S. Appl. No. 16/527,926, dated May 11, 2021 (Non-Final Rejection).

U.S. Office Action for U.S. Appl. No. 16/527,926, dated Sep. 17, 2021 (Final Rejection).

ULTRASOUND DIAGNOSTIC APPARATUS, METHOD FOR CONTROLLING ULTRASOUND DIAGNOSTIC APPARATUS, AND READABLE RECORDING MEDIUM RECORDING A PROGRAM FOR CONTROLLING ULTRASOUND DIAGNOSTIC APPARATUS

CROSS-REFERENCE TO RELATED APPLICATIONS

This application is a Divisional of copending application Ser. No. 16/527,926, filed on Jul. 31, 2019, which is a Continuation of PCT International Application No. PCT/JP2018/001347 filed on Jan. 18, 2018, which claims priority under 35 U.S.C. § 119(a) to Japanese Patent Application No. 2017-016578 filed on Feb. 1, 2017. Each of the above applications are hereby expressly incorporated by reference, in their entirety, into the present application.

BACKGROUND OF THE INVENTION

1. Field of the Invention

The present invention relates to an ultrasound diagnostic apparatus, a method for controlling an ultrasound diagnostic apparatus, and a readable recording medium recording a program for controlling an ultrasound diagnostic apparatus, and more particularly, to an ultrasound diagnostic apparatus that determines an imaging part of a subject, a method for controlling the ultrasound diagnostic apparatus, and a readable recording medium recording a program for controlling the ultrasound diagnostic apparatus.

2. Description of the Related Art

In recent years, an ultrasound diagnostic apparatus has been known as an apparatus for obtaining an image of the inside of a subject. In general, the ultrasound diagnostic apparatus comprises an ultrasound probe comprising a transducer array in which a plurality of elements are arranged. In a state in which the ultrasound probe is in contact with the body surface of the subject, ultrasound beams are transmitted from the transducer array to the subject and the transducer array receives ultrasound echoes from the subject. In this way, element data is acquired. In addition, the ultrasound diagnostic apparatus electrically processes the obtained element data to generate an ultrasound image of a corresponding part of the subject.

It has been known that, in a case in which the ultrasound image of a part of the subject is generated by the ultrasound diagnostic apparatus, there are imaging conditions suitable for each part. It is preferable that the imaging conditions are automatically set in a case in which the ultrasound image of each part is generated. However, it is necessary to automatically determine an imaging part of the subject which is currently being examined in order to automatically set the imaging conditions.

Therefore, various proposals have been made as the ultrasound diagnostic apparatus that can automatically determine an imaging part of a subject. For example, an ultrasound diagnostic apparatus disclosed in JP1992-224738A (JP-H04-224738A) includes a pattern memory that stores characteristic patterns of each part of a subject, collates an image pattern extracted from a generated ultrasound image with a plurality of pattern data items stored in the pattern memory, detects pattern data similar to the image pattern included in the generated ultrasound image, and determines an imaging part.

SUMMARY OF THE INVENTION

However, in general, the amount of calculation load required for image recognition that extracts an image pattern from a generated ultrasound image and collates the extracted image pattern with pattern data stored in advance is large. In particular, in a case in which the image recognition is performed by an apparatus with a low processing performance, it takes a lot of time until the image recognition is completed. In addition, in the ultrasound diagnostic apparatus disclosed in JP1992-224738A (JP-H04-224738A), in a case in which the image recognition is performed for a plurality of parts of the subject, it is necessary to collate the image pattern extracted from the generated ultrasound image with many pattern data items corresponding to the plurality of parts. As a result, the time required to determine the imaging part further increases. In addition, in the ultrasound diagnostic apparatus disclosed in JP1992-224738A (JP-H04-224738A), this process needs to be performed for each of the plurality of parts of the subject.

The invention has been made in order to solve the problems of the related art and an object of the invention is to provide an ultrasound diagnostic apparatus that can reduce the time required to determine an imaging part, a method for controlling the ultrasound diagnostic apparatus, and a readable recording medium recording a program for controlling the ultrasound diagnostic apparatus.

In order to achieve the object, an ultrasound diagnostic apparatus according to the invention comprises: an image acquisition unit that transmits an ultrasound beam from an ultrasound probe to a subject to generate an ultrasound image; an image recognition unit that performs image recognition for the ultrasound image generated by an image acquisition unit to calculate recognition scores of a plurality of parts of the subject; an index value calculation unit that calculates index values of the plurality of parts on the basis of the recognition scores of the plurality of parts calculated for a predetermined number of ultrasound images; a part narrowing-down unit that narrows down target parts for which part determination is to be performed, from the plurality of parts on the basis of the index values; and a part determination unit that determines an imaging part of the subject on the basis of the recognition scores calculated by the image recognition unit for the target parts narrowed down by the part narrowing-down unit.

Preferably, the index value calculation unit uses, as the index values of the plurality of parts, recognition scores of the plurality of parts calculated by the image recognition unit for a latest ultrasound image acquired by the image acquisition unit.

The index value calculation unit may calculate the index values of the plurality of parts using recognition scores of the plurality of parts calculated by the image recognition unit for each of a plurality of ultrasound images which are continuously acquired in time series and include a latest ultrasound image acquired by the image acquisition unit.

Preferably, the index value calculation unit uses mean values or medians of the recognition scores of the plurality of parts calculated for the plurality of ultrasound images, as the index values of the plurality of parts.

The index value calculation unit may use maximum values or minimum values of the recognition scores of the plurality of parts calculated for the plurality of ultrasound images, as the index values of the plurality of parts.

The index value calculation unit may calculate weighted mean values of the recognition scores of the plurality of parts by giving a larger weight to an ultrasound image more recently acquired by the image acquisition unit among the plurality of ultrasound images, and may use the weighted mean values as the index values of the plurality of parts.

The index value calculation unit may give ranking scores to the plurality of parts for each of the plurality of ultrasound images such that the part with a higher recognition score has a higher ranking score, and may use sums of the ranking scores of the plurality of parts for the plurality of ultrasound images, as the index values of the plurality of parts.

The index value calculation unit may have a threshold value of the recognition score, and may use the number of recognition scores greater than the threshold value among the recognition scores of the plurality of parts calculated for the plurality of ultrasound images, as the index value of each of the plurality of parts.

Preferably, the ultrasound diagnostic apparatus further comprises a probe state detection unit that detects a change in an imaging part caused by movement of the ultrasound probe. Preferably, the index value calculation unit starts to calculate the index value after the probe state detection unit detects the change in the imaging part.

Preferably, the part narrowing-down unit has a narrowing-down threshold value for the index value, and narrows down the plurality of parts of the subject having the index value greater than the narrowing-down threshold value, as the target parts.

Preferably, the ultrasound diagnostic apparatus further comprises an order decision unit that decides a determination order in which part determination is performed for the plurality of parts, on the basis of the index values. Preferably, the order decision unit decides the determination order such that the part with a larger index value is ranked higher.

Preferably, in a case in which the imaging part is not decided for all of the target parts narrowed down by the part narrowing-down unit, the part determination unit determines the imaging part for the parts other than the target parts among the plurality of parts.

According to the invention, there is provided a method for controlling an ultrasound diagnostic apparatus. The method comprises: transmitting an ultrasound beam from an ultrasound probe to a subject to generate an ultrasound image; performing image recognition for the ultrasound image to calculate recognition scores of a plurality of parts of the subject; calculating index values of the plurality of parts on the basis of the recognition scores of the plurality of parts calculated for a predetermined number of ultrasound images; narrowing down target parts for which part determination is to be performed, from the plurality of parts on the basis of the index values; and determining an imaging part of the subject on the basis of the calculated recognition scores for the narrowed-down target parts.

According to the invention, there is provided a readable recording medium recording a program for controlling an ultrasound diagnostic apparatus. The program comprises: a step of transmitting an ultrasound beam from an ultrasound probe to a subject to generate an ultrasound image; a step of performing image recognition for the ultrasound image to calculate recognition scores of a plurality of parts of the subject; a step of calculating index values of the plurality of parts on the basis of the recognition scores of the plurality of parts calculated for a predetermined number of ultrasound images; a step of narrowing down target parts for which part determination is to be performed, from the plurality of parts on the basis of the index values; and a step of determining an imaging part of the subject on the basis of the calculated recognition scores for the narrowed-down target parts.

According to the invention, the ultrasound diagnostic apparatus includes the part narrowing-down unit that narrows down the target parts for which the part determination is to be performed, and determines the imaging part of the subject for the narrowed-down target parts. Therefore, it is possible to reduce the time required to determine the imaging part.

DESCRIPTION OF THE PREFERRED EMBODIMENTS

Hereinafter, embodiments of the invention will be described with reference to the accompanying drawings.

Embodiment 1

Figure 1:
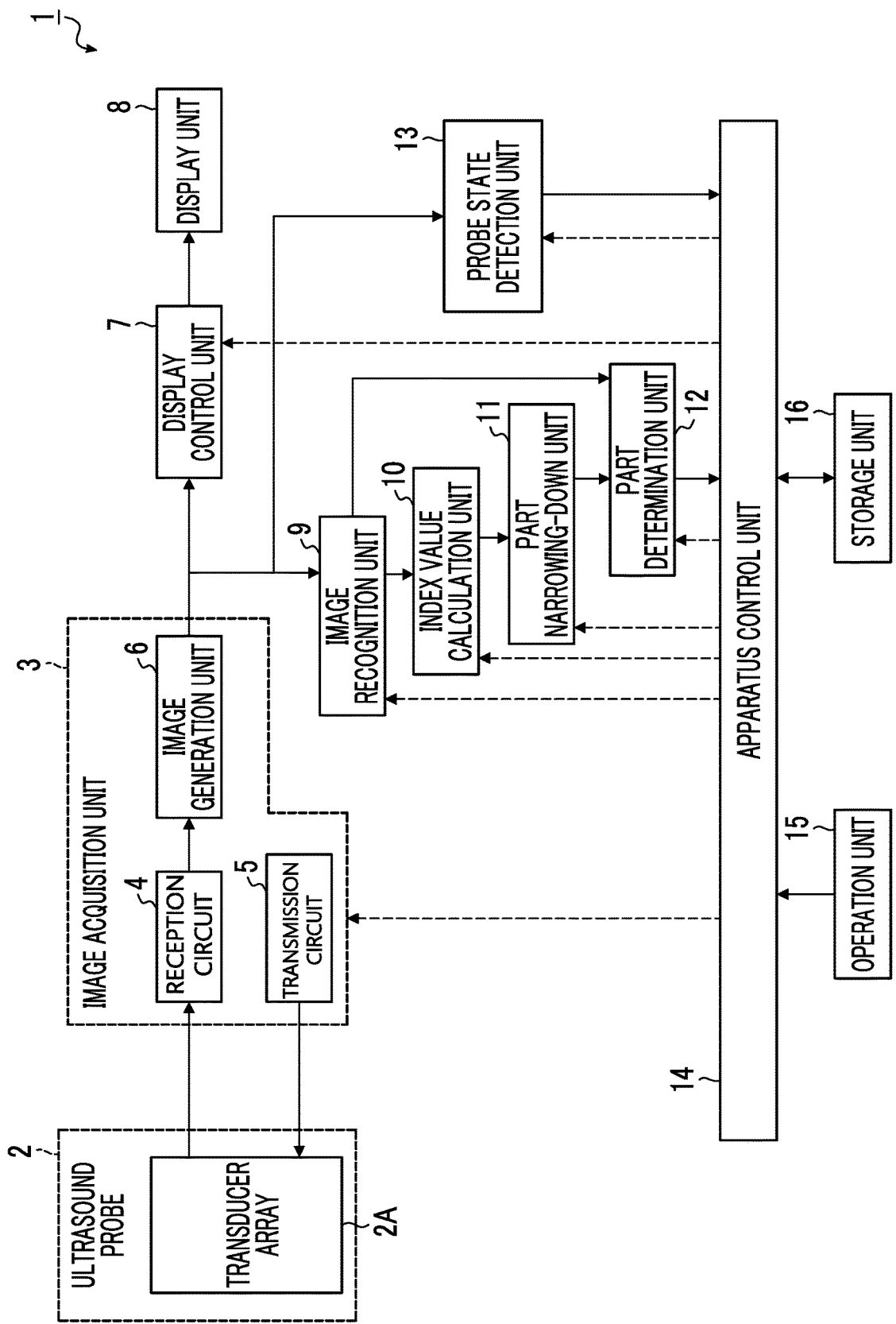
FIG. 1 is a block diagram illustrating the configuration of an ultrasound diagnostic apparatus according to Embodiment 1 of the invention.

FIG. 1 illustrates the configuration of an ultrasound diagnostic apparatus according to Embodiment 1 of the invention. An ultrasound diagnostic apparatus 1 comprises an ultrasound probe 2 provided with a transducer array 2A. A display control unit 7 and a display unit 8 are sequentially connected to the ultrasound probe 2 through an image acquisition unit 3.

The image acquisition unit 3 includes a receiving unit 4 and a transmitting unit 5 that are connected to the transducer array 2A of the ultrasound probe 2, and an image generation unit 6 that is connected to the receiving unit 4. The display control unit 7 is connected to the image generation unit 6. In addition, an image recognition unit 9 is connected to the image generation unit 6. An index value calculation unit 10 is connected to the image recognition unit 9. A part narrowing-down unit 11 is connected to the index value calculation unit 10. A part determination unit 12 is connected to the part narrowing-down unit 11. Further, the image recognition unit 9 is connected to the part determination unit 12. Furthermore, a probe state detection unit 13 is connected to the image generation unit 6.

In addition, an apparatus control unit 14 is connected to the image acquisition unit 3, the display control unit 7, the image recognition unit 9, the index value calculation unit 10, the part narrowing-down unit 11, the part determination unit 12, and the probe state detection unit 13. An operation unit 15 and a storage unit 16 are connected to the apparatus control unit 14. The apparatus control unit 14 and the storage unit 16 are connected such that information can be bi-directionally transmitted and received therebetween.

The transducer array 2A of the ultrasound probe 2 illustrated in FIG. 1 includes a plurality of elements (ultrasound transducers) which are one-dimensionally or two-dimensionally arranged. Each of the elements transmits ultrasonic waves in response to a driving signal supplied from the transmitting unit 5. In addition, each of the elements receives ultrasound echoes from a subject and outputs a received signal. Each of the elements is, for example, a transducer in which electrodes are formed at both ends of a piezoelectric body made of piezoelectric ceramic typified by lead zirconate titanate (PZT), a polymer piezoelectric element typified by polyvinylidene difluoride (PVDF), or a piezoelectric single crystal typified by lead magnesium niobate-lead titanate (PMN-PT).

In a case in which a pulsed voltage or a continuous-wave voltage is applied to the electrodes of the transducer, the piezoelectric body is expanded and contracted and pulsed or continuous ultrasonic waves are generated from each transducer. The ultrasonic waves are combined to form an ultrasound beam. In addition, each transducer receives propagated ultrasonic waves, is expanded and contracted, and generates an electric signal. The electric signal is output as a received ultrasound signal from each transducer to the receiving unit 4.

Figure 2:
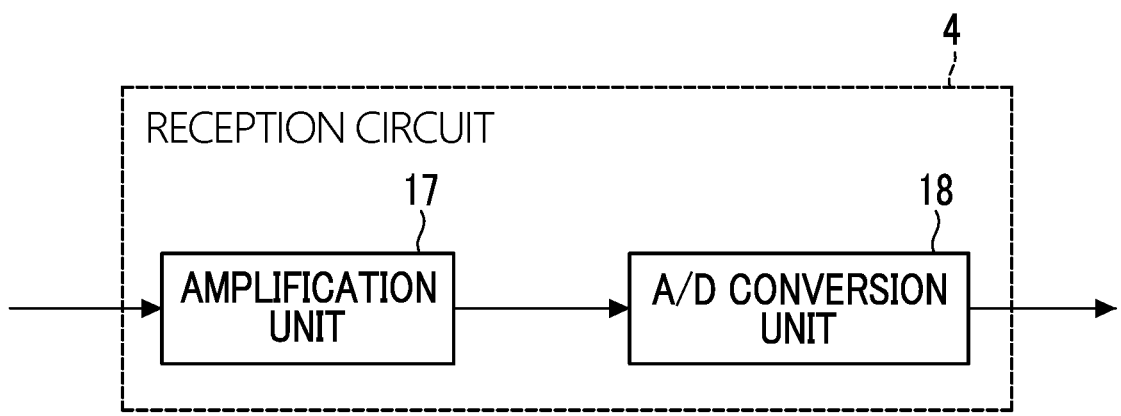
FIG. 2 is a block diagram illustrating the internal configuration of a receiving unit illustrated in FIG. 1.

As illustrated in FIG. 2, the receiving unit 4 of the image acquisition unit 3 has a configuration in which an amplification unit 17 and an analog/digital (A/D) conversion unit 18 are connected in series to each other. The receiving unit 4 outputs, to the image generation unit 6, element data obtained by amplifying the received signal output from each element of the transducer array 2A with the amplification unit 17 and converting the amplified signal into a digital signal with the A/D conversion unit 18.

The transmitting unit 5 of the image acquisition unit 3 includes, for example, a plurality of pulse generators, adjusts the amount of delay of each driving signal such that the ultrasonic waves transmitted from the plurality of elements of the transducer array 2A form an ultrasound beam, on the basis of a transmission delay pattern selected according to a control signal from the apparatus control unit 14, and supplies the driving signals to the plurality of elements.

Figure 3:
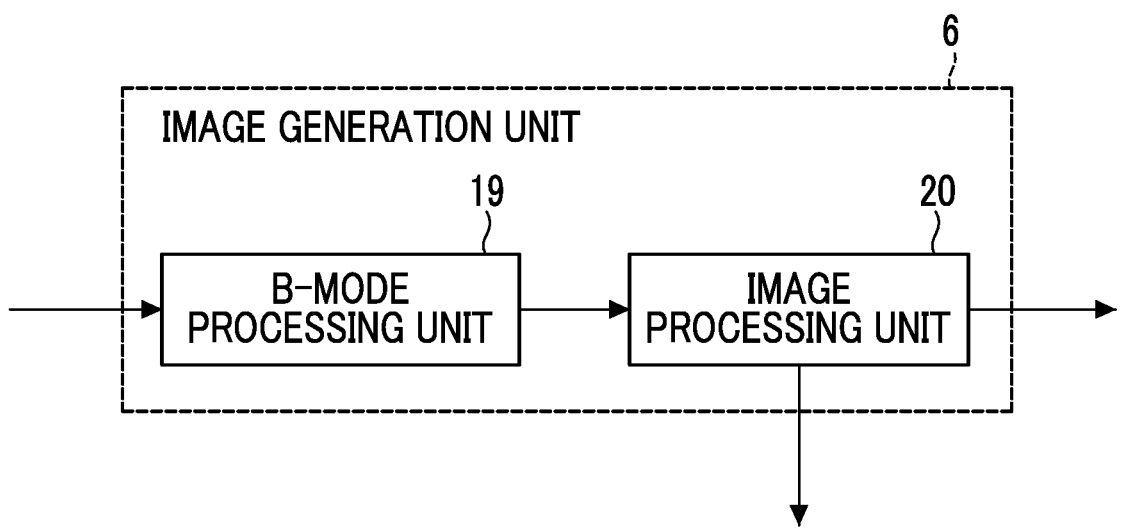
FIG. 3 is a block diagram illustrating the internal configuration of an image generation unit illustrated in FIG. 1.

As illustrated in FIG. 3, the image generation unit 6 of the image acquisition unit 3 has a configuration in which a brightness-mode (B-mode) processing unit 19 and an image processing unit 20 are sequentially connected in series to each other.

The B-mode processing unit 19 performs a reception focusing process which applies a delay to each element data item following a set sound speed on the basis of a reception delay pattern selected according to a control signal from the apparatus control unit 14 and adds the received data (phasing addition). A sound ray signal in which the focus of the ultrasound echo is narrowed is generated by the reception focusing process. In addition, the B-mode processing unit 19 corrects the attenuation of the sound ray signal caused by a propagation distance according to the depth of the reflection position of ultrasonic waves and then performs an envelope detection process to generate a B-mode image signal which is tomographic image information related to the tissues in the subject. The B-mode image signal generated by the B-mode processing unit 19 is output to the image processing unit 20.

The image processing unit 20 converts the B-mode image signal generated by the B-mode processing unit 19 into an image signal based on a general television signal scanning system (raster conversion), performs various types of necessary image processing, such as a gradation process, for the B-mode image signal, and outputs a B-mode image signal, that is, an ultrasound image to the display control unit 7 and the image recognition unit 9.

As illustrated in FIG. 1, the display control unit 7 of the ultrasound diagnostic apparatus 1 directs the display unit 8 to display the ultrasound image on the basis of the B-mode image signal acquired by the image acquisition unit 3.

The display unit 8 includes a display device, such as a liquid crystal display (LCD), and displays the ultrasound image under the control of the apparatus control unit 14.

The image recognition unit 9 receives the ultrasound image subjected to various types of image processing from the image processing unit 20 of the image generation unit 6 and performs image recognition, such as pattern recognition, for the ultrasound image to calculate recognition scores of a plurality of parts of the subject. Here, the recognition scores of the plurality of parts of the subject are the similarities of imaging parts in the ultrasound image to the plurality of parts of the subject. As the value of the similarity becomes larger, the probability of the imaging part in the ultrasound image being the corresponding part becomes higher.

The index value calculation unit 10 calculates the index values of the plurality of parts of the subject on the basis of the recognition scores of the plurality of parts of the subject calculated by the image recognition unit 9. There are various methods for calculating the index values. Hereinafter, for the purpose of description, it is assumed that the index values of the plurality of parts of the subject are the mean values of the recognition scores of the plurality of parts of the subject calculated for a plurality of ultrasound images. As such, in a case in which the index values are calculated on the basis of the recognition scores for a plurality of ultrasound images, the index value calculation unit 10 calculates the index values on the basis of the recognition scores for a plurality of ultrasound images which are continuously acquired in time series and include the latest ultrasound image acquired by the image acquisition unit 3.

The part narrowing-down unit 11 decides a part as a determination target of the imaging part among the plurality of parts of the subject, on the basis of the index values of the plurality of parts of the subject calculated by the index value calculation unit 10. At that time, the part narrowing-down unit 11 narrows down the parts having index values greater than a narrowing-down threshold value, as the determination target of the imaging part. Here, the narrowing-down threshold value is a threshold value for the index value, which is set for narrowing down the parts.

The part determination unit 12 determines the imaging part of the subject for the ultrasound image acquired by the image acquisition unit 3 on the basis of the recognition scores calculated by the image recognition unit 9. At that time, the part determination unit 12 sequentially determines the imaging part from the part that is ranked first according to a predetermined order, for the parts narrowed down by the part narrowing-down unit 11. Here, for the purpose of description, in Embodiment 1, it is assumed that a determination order of the part determination unit 12 for the plurality of parts of the subject is determined in advance by an input or the like by an operator through the operation unit 15.

The probe state detection unit 13 determines whether the ultrasound probe 2 is in an aerial emission state. Here, the aerial emission state of the ultrasound probe 2 means a state in which the ultrasound probe 2 is separated from the body surface of the subject and the ultrasound beam transmitted from the transducer array 2A to the subject is emitted to the air. In a case in which the ultrasound probe 2 is in the aerial emission state, the ultrasound beam emitted from the transducer array 2A is not reflected from a part of the subject and the received signal generated in the transducer array 2A does not have sufficient intensity. As a result, the image of the part is not included in the ultrasound image generated by the image generation unit 6. Therefore, the probe state detection unit 13 determines that the ultrasound probe 2 is in the aerial emission state in a case in which no image is included in the ultrasound image and determines that the ultrasound probe 2 is in contact with the subject in a case in which an image is included in the ultrasound image.

The apparatus control unit 14 controls each unit of the ultrasound diagnostic apparatus 1 on the basis of commands input by an operator through the operation unit 15.

The operation unit 15 is used by the operator to perform an input operation and may include, for example, a keyboard, a mouse, a trackball, and a touch panel.

The storage unit 16 stores, for example, an operation program of the ultrasound diagnostic apparatus 1 and may be a recording medium, such as a hard disc drive (HDD), a solid state drive (SSD), a flexible disc (FD), a magneto-optical (MO) disc, a magnetic tape (MT), a random access memory (RAM), a compact disc (CD), a digital versatile disc (DVD), a secure digital (SD) card, or a universal serial bus (USB) memory, or a server.

The image generation unit 6 of the image acquisition unit 3, the display control unit 7, the image recognition unit 9, the index value calculation unit 10, the part narrowing-down unit 11, the part determination unit 12, the probe state detection unit 13, and the apparatus control unit 14 are implemented by a central processing unit (CPU) and a control program that causes the CPU to perform various processes. However, these units may be implemented by a digital circuit and a computer. In addition, some or all of the image generation unit 6, the display control unit 7, the image recognition unit 9, the index value calculation unit 10, the part narrowing-down unit 11, the part determination unit 12, the probe state detection unit 13, and the apparatus control unit 14 may be integrated into one CPU.

Next, the operation of the ultrasound diagnostic apparatus 1 according to Embodiment 1 will be described with reference to a flowchart illustrated in FIG. 4.

First, in Step S1, the receiving unit 4 and the transmitting unit 5 of the image acquisition unit 3 perform the transmission and reception of ultrasound beams and scanning, that is, the capture of an ultrasound image, using the plurality of ultrasound transducers of the transducer array 2A in the ultrasound probe 2. At that time, each ultrasound transducer which has received ultrasound echoes from the subject generates a received signal and the received signal is input to the receiving unit 4. The amplification unit 17 of the receiving unit 4 amplifies the received signal input to the receiving unit 4. In addition, the A/D conversion unit 18 performs A/D conversion for the received signal. Furthermore, the received signal is input to the image generation unit 6. The B-mode processing unit 19 of the image generation unit 6 generates a B-mode image, that is, an ultrasound image.

Then, in Step S2, the probe state detection unit 13 determines whether the ultrasound probe 2 is in the aerial emission state. In a case in which it is determined in Step S2 that the ultrasound probe 2 is in the aerial emission state, the process returns to Step S1. On the other hand, in a case in which it is determined in Step S2 that the ultrasound probe 2 is not in the aerial emission state and is in contact with the body surface of the subject, the process proceeds to Step S3.

In Step S3, the part determination is performed for the imaging part that is currently being examined. The part determination in Step S3 will be described in detail below with reference to FIG. 5.

In a case in which the imaging part is determined in Step S3, the process proceeds to Step S4. In Step S4, the apparatus control unit 14 sets imaging conditions suitable for the part determined in Step S3. Here, the imaging conditions include, for example, a frame rate in ultrasound diagnosis, the resolution of an ultrasound image, the brightness of an ultrasound image, and a dynamic range in ultrasound diagnosis.

Then, in Step S5, the image acquisition unit 3 acquires an ultrasound image. At that time, since the imaging conditions set in Step S4 are used as the imaging conditions, the image acquisition unit 3 can acquire the ultrasound image in which the image of the imaging part is clear.

Then, in Step S6, it is determined again whether the ultrasound probe 2 is in the aerial emission state. Here, in a case in which the probe state detection unit 13 determines that the ultrasound probe 2 is not in the aerial emission state and is in contact with the body surface of the subject, it is determined that the imaging part has not been changed and the process returns to Step S5 to acquire an ultrasound image again. On the other hand, in a case in which the probe state detection unit 13 determines that the ultrasound probe 2 is in the aerial emission state, it is determined that a change in the imaging part has started and the process returns to Step S1.

Next, the part determination in Step S3 will be described with reference to FIG. 5. In a case in which the part determination in Step S3 starts, first, an ultrasound image is acquired in Step S7.

Then, in Step S8, the image recognition unit 9 calculates the recognition scores of a plurality of parts of the subject for the ultrasound image acquired in Step S7.

Then, in Step S9, the apparatus control unit 14 determines whether the recognition scores of a plurality of parts of the subject have been calculated for a predetermined number of frames of ultrasound images. Here, the part determination process in Step S3 has the determination step of Step S9 in order to obtain the number of recognition scores required for the index value calculation unit 10 to calculate the index values. Therefore, in a case in which it is determined in Step S9 that the recognition scores have not been calculated for a predetermined number of frames of ultrasound images, the process returns to Step S7 to acquire an ultrasound image. Then, in Step S8, a recognition score is calculated for a new ultrasound image. As such, as a result of the repetition of Steps S7 and S8, in a case in which it is determined in Step S9 that the recognition scores of a plurality of parts of the subject have been calculated for a predetermined number of frames of ultrasound images, the process proceeds to Step S10.

In Step S10, the index value calculation unit 10 averages a predetermined number of recognition scores calculated by the repetition of Steps S7 and S8 for each of a plurality of parts to calculate the index values of the plurality of parts of the subject.

Then, in Step S11, the part narrowing-down unit 11 narrows down, as a determination target part of the imaging part, the parts having index values, which are calculated in Step S10, greater than the narrowing-down threshold value from among the plurality of parts of the subject. For example, in a case in which the plurality of parts of the subject include the heart and the lung, the index value of the heart is greater than the narrowing-down threshold value, and the index value of the lung is equal to or lower than the narrowing-down threshold value, the heart remains as the determination target part and the lung is excluded from the determination target part. Hereinafter, for the purpose of description, the determination target parts which are narrowed down in Step S11 from among the plurality of parts of the subject are referred to as target parts.

Then, in Step S12, in a case in which the image acquisition unit 3 acquires a new ultrasound image, the process proceeds to Step S13.

In Step S13, the image recognition unit 9 calculates the recognition score of the part that is ranked first according to the decided determination order among the determination target parts narrowed down in Step S11, for the latest ultrasound image acquired in Step S12. For example, in a case in which the plurality of parts of the subject include the heart, the lung, and the right abdominal area, and are ranked in advance such that the heart is ranked first, the lung is ranked second, and the right abdominal area is ranked third, and the heart and the right abdominal area are narrowed down as the determination target part in Step S11, the heart is ranked first and the right abdominal area is ranked second. Therefore, in this case, the recognition score of the heart is calculated.

Then, in Step S14, the part determination unit 12 performs threshold value determination of whether the recognition score of one part calculated in Step S13 is greater than a determination threshold value. The determination threshold value is the threshold value of the recognition score in part determination, and the same determination threshold value can be used for all of the parts. In a case in which it is determined in Step S14 that the recognition score of one part is equal to or less than the determination threshold value, it is determined that it is difficult to decide the imaging part as the part whose recognition score has been calculated in Step S13, and the process proceeds to Step S15.

In Step S15, the apparatus control unit 14 determines whether the threshold value determination for the recognition scores of all of the parts among the target parts narrowed down in Step S11 has been performed in Step S14. Further, in a case in which it is determined in Step S15 that the threshold value determination for the recognition scores of all of the narrowed-down target parts has not been performed in Step S14, the process proceeds to Step S16.

In Step S16, the apparatus control unit 14 updates a determination part. That is, the apparatus control unit 14 changes the part, of which the recognition score is to be calculated in the next Step S13, from the part that is ranked first to the part that is ranked second in the decided determination order, among the parts narrowed down in Step S11. Hereinafter, for the purpose of description, the ranked part for which the determination in Step S14 is to be performed, among the plurality of parts of the subject is referred to as the determination part. In a case in which the determination part is updated, the process returns to Step S13 in order to determine the imaging part for the next part on the basis of the determination order.

In Step S13 performed for the second time, only the recognition score of the part that is ranked second in the decided determination order decided among the parts narrowed down in Step S11 is calculated for the ultrasound image acquired in Step S12. Then, in Step S14, the part determination unit 12 determines whether the recognition score of the part that is ranked second in the determination order is greater than the determination threshold value. Here, in a case in which it is determined that the recognition score is equal to or less than the determination threshold value, the process proceeds to Step S15.

As such, as long as it is determined in Step S14 that the recognition score of the determination part is equal to or less than the determination threshold value, Steps S13 to S16 are repeated for the target parts narrowed down in Step S11, according to the determination order decided in Step S11. In a case in which it is determined in Step S15 that the threshold value determination for the recognition scores of all of the target parts narrowed down in Step S11 has been performed in Step S14 as a result of the repetition of Steps S13 to S16, it is determined that it is difficult to decide the part included in the ultrasound image acquired in Step S12 to be any of the plurality of parts of the subject, and the process returns to Step S8. In the subsequent Steps S8 to S14, the index values of the plurality of parts of the subject are newly calculated on the basis of the newly calculated recognition scores of the plurality of parts of the subject, and the determination target parts of the imaging part are newly narrowed down on the basis of the index values. In addition, the recognition scores are calculated for the ultrasound image newly acquired in Step S12 according to the decided determination order of the narrowed-down parts, and part determination is performed for the imaging part on the basis of the recognition scores.

In a case in which it is determined in Step S14 that the recognition score of the determination part is greater than the determination threshold value, the process proceeds to Step S17.

In Step S17, the part determination unit 12 decides the imaging part whose image is currently captured, as the determination part having the recognition score that is determined to be greater than the determination threshold value in Step S14. Then, the part determination operation ends.

In the ultrasound diagnostic apparatus 1 according to Embodiment 1 described above, in a case in which part determination is performed, the parts with a high probability of being the imaging part whose image is currently captured are narrowed down as the part, which is the target of the part determination, for the imaging part, and a plurality of parts of the subject are sequentially determined according to the decided determination order for the narrowed-down parts. Therefore, it is possible to reduce the calculation load of the ultrasound diagnostic apparatus 1 and to reduce the time required to determine the imaging part.

The index value calculation unit 10 averages the recognition scores of the plurality of parts of the subject calculated for a plurality of ultrasound images to calculate the index values of the plurality of parts of the subject. However, for example, the number of ultrasound images required for the index value calculation unit 10 to calculate the index value may be set by the operator through the operation unit 15 or the like, or may be stored in the index value calculation unit 10 and the storage unit 16 in advance.

In addition, the index value calculation unit 10 may calculate the index value using various methods other than the method of averaging the recognition scores of each of the plurality of parts of the subject. For example, the index value calculation unit 10 may use the medians of the recognition scores of the plurality of parts of the subject calculated for a plurality of ultrasound images as the index values of the plurality of parts of the subject.

In addition, for example, the index value calculation unit 10 may use the maximum values of the recognition scores of the plurality of parts of the subject calculated for a plurality of ultrasound images, as the index values of the plurality of parts of the subject. Further, the index value calculation unit 10 may use the minimum values of the recognition scores of the plurality of parts of the subject calculated for a plurality of ultrasound images, as the index values of the plurality of parts of the subject.

Furthermore, for example, the index value calculation unit 10 may use weighted mean values obtained by weighting and averaging the recognition scores of the plurality of parts of the subject calculated for a plurality of ultrasound images, as the index values of the plurality of parts of the subject. In this case, the index value calculation unit 10 may calculate the weighted mean value by giving a larger weight to the recognition score calculated for an ultrasound image more recently acquired by the image acquisition unit 3 among the plurality of ultrasound images.

For example, the index value calculation unit 10 may give ranking scores to a plurality of parts of the subject for each of a plurality of ultrasound images such that the ranking score becomes higher as the recognition score becomes higher. In this case, the index value calculation unit 10 can use the sums of the ranking scores of the plurality of parts of the subject for the plurality of ultrasound images, as the index values of the plurality of parts of the subject. That is, for example, for each ultrasound image, the ranking scores are given to the plurality of parts of the subject such that a higher score is given to the part with a higher recognition score in the order of five points, four points, three points, two points, and one point, and the ranking scores of each part for the plurality of ultrasound images are added up to calculate the index values of the plurality of parts of the subject.

In addition, for example, the index value calculation unit 10 may have a threshold value of the recognition score, and calculate the index value from the result of threshold value determination for the recognition score. In this case, the index value calculation unit 10 can use the number of recognition scores that are greater than the threshold value among the recognition scores of the plurality of parts of the subject calculated for the plurality of ultrasound images, as the index values of the plurality of parts of the subject. That is, for example, in a case in which the number of recognition scores that are greater than the threshold value among the recognition scores of the heart calculated for the plurality of ultrasound images is 3, the index value calculation unit 10 can set the index value of the heart to 3.

As described above, the index value calculation unit 10 can calculate the index values on the basis of the recognition scores calculated for a plurality of frames of ultrasound images. However, the index value calculation unit 10 may use the recognition scores calculated for one frame of ultrasound image as the index values. For example, the index value calculation unit 10 can use the recognition scores of the plurality of parts of the subject calculated only for the latest ultrasound image acquired by the image acquisition unit 3, as the index values of the plurality of parts of the subject.

In the above description, in a case in which no image is included in the acquired ultrasound image, the probe state detection unit 13 determines that the ultrasound probe 2 is in the aerial emission state. However, the probe state detection unit 13 may compare a plurality of ultrasound images acquired in time series to determine whether the ultrasound probe 2 is in the aerial emission state. That is, the probe state detection unit 13 may compare a plurality of ultrasound images acquired in time series and may determine that, in a case in which there is no change in the images included in the plurality of ultrasound images between the plurality of ultrasound image, the ultrasound probe 2 is not in contact with the body surface, thereby determining that the ultrasound probe 2 is in the aerial emission state. In addition, in a case in which there is a change in the images included in the plurality of ultrasound images acquired in time series between the plurality of ultrasound images, the probe state detection unit 13 may determine that a part of the subject is included in the plurality of ultrasound images, thereby determining that the ultrasound probe 2 is in contact with the body surface of the subject.

With this configuration, even in the case in which ultrasonography gel is attached to the ultrasound probe 2, the probe state detection unit 13 can compare a plurality of ultrasound images acquired in time series to determine whether the ultrasound probe 2 is in the aerial emission state.

Figure 4:
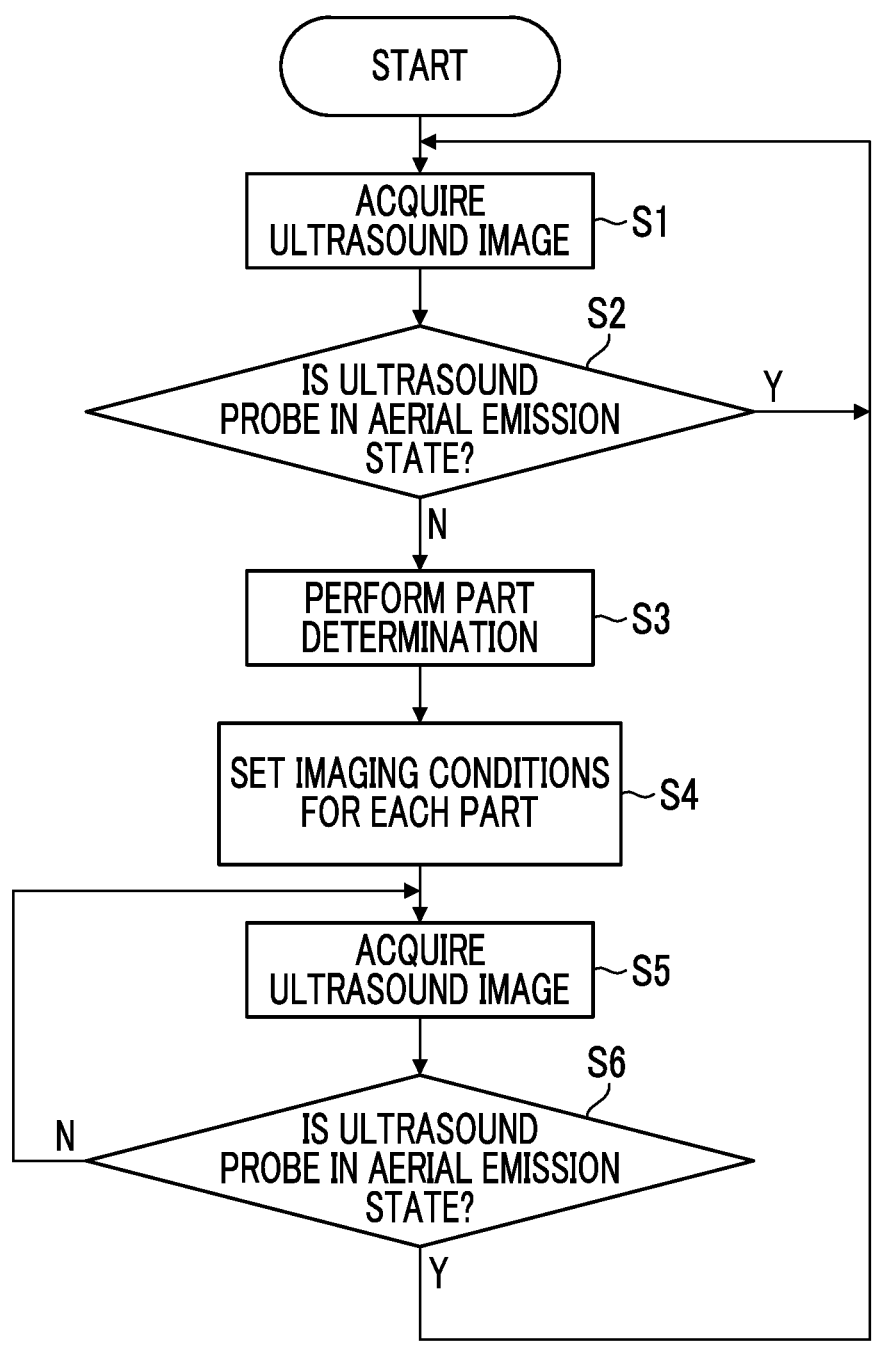
FIG. 4 is a flowchart illustrating an operation of the ultrasound diagnostic apparatus according to Embodiment 1 of the invention.

In the flowchart illustrated in FIG. 4, in a case in which the probe state detection unit 13 detects a change in the imaging part, the part determination in Step S3 starts. This means that, in a case in which the probe state detection unit 13 detects a change in the imaging part, the index value calculation unit 10 starts to calculate the index value on the basis of the recognition score calculated for a newly acquired ultrasound image. As such, it is possible to reduce the calculation load of the ultrasound diagnostic apparatus 1 by calculating the index value for the ultrasound image only while the ultrasound probe 2 is in contact with the body surface of the subject. In addition, in a case in which the index value calculation unit 10 calculates the index values, it is possible to prevent the index value calculation unit 10 from using the recognition scores of the previous imaging part.

In addition, the index value calculation unit 10 may start to calculate the index values for the plurality of parts of the subject after a predetermined period of time has elapsed since the probe state detection unit 13 has detected a change in the imaging part. For example, the time until the index value calculation unit 10 calculates the index values of the plurality of parts of the subject after the probe state detection unit 13 detects a change in the imaging part may be input by the operator through the operation unit 15 or the like, or may be stored in advance in the storage unit 16.

The time until the ultrasound probe 2 is brought into contact with the body surface of the subject to obtain the ultrasound image of a target imaging part varies depending on, for example, the skill of the operator. In some cases, immediately after the imaging part is changed, an ultrasound image that is sufficiently clear to calculate the recognition score is not obtained. For this reason, in a case in which the calculation of the index values of a plurality of parts of the subject starts after a predetermined period of time has elapsed since the probe state detection unit 13 has detected a change in the imaging part, it is possible to calculate the index values on the basis of a plurality of recognition scores calculated for the ultrasound image that is sufficiently clear. Therefore, it is possible to improve the accuracy of calculating the index value.

Figure 5:
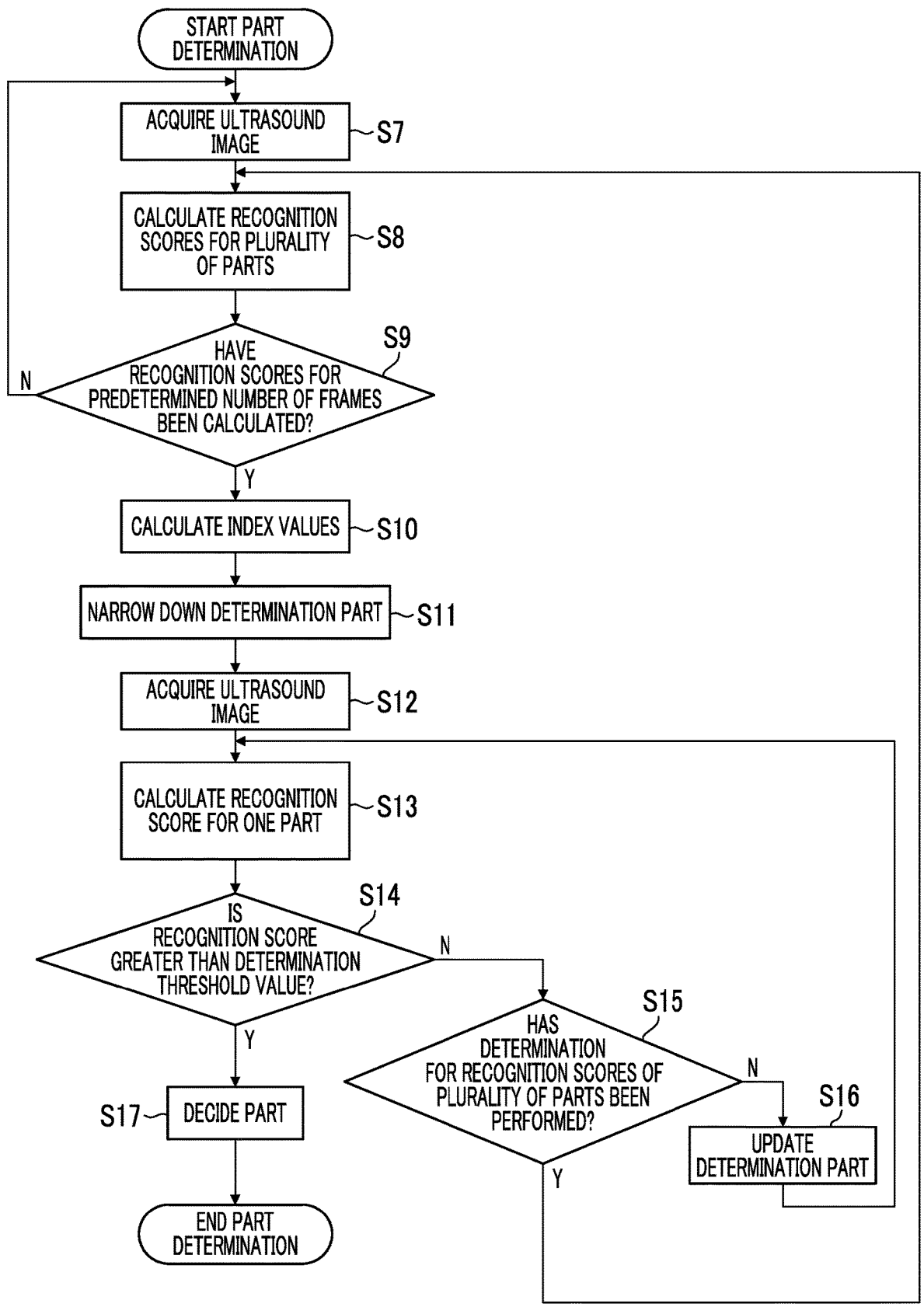
FIG. 5 is a flowchart illustrating a part determination operation of the ultrasound diagnostic apparatus according to Embodiment 1 of the invention.

In addition, in the flowchart illustrated in FIG. 5, Steps S12 and S13 may be omitted. In that case, in a case in which the target parts which are the targets for the determination of the imaging part are narrowed down in Step S11, the process proceeds to Step S14. In Step S14, the part determination unit 12 compares the recognition score of the part that is ranked first in the decided determination order among the recognition scores of the plurality of parts of the subject calculated in Step S8 for the latest ultrasound image acquired in Step S7 with the determination threshold value. At that time, in a case in which the recognition score is equal to or less than the determination threshold value, the process proceeds to Step S15. Further, in a case in which it is determined in Step S15 that the threshold value determination for the recognition scores of all of the target parts narrowed down in Step S11 has not been performed, the process proceeds to Step S16. In a case in which the determination part is updated in Step S16, it is determined in Step S14 whether the recognition score of the part that is ranked second in the determination order is greater than the determination threshold value.

In the above-described embodiment, the same determination threshold value is used for all of the parts by the part determination unit 12 in Step S14. However, the determination threshold value may be set for each of the plurality of parts of the subject.

The above-mentioned ultrasound diagnostic apparatus 1 may be a portable ultrasound diagnostic apparatus that is small and can be easily carried and used or a stationary ultrasound diagnostic apparatus that is installed and used in, for example, a medical examination room.

In addition, the ultrasound probe 2 is not particularly limited as long as it can transmit and receive ultrasound beams to and from the subject and may be a sector type, a convex type, a linear type, or a radial type.

Embodiment 2

In the operation of the ultrasound diagnostic apparatus 1 illustrated in the flowchart of FIG. 4, in a case in which the ultrasound probe 2 is in the aerial emission state in Step S6, the process returns to Step S1. Then, in Step S3, the part determination is performed for all of the plurality of parts of the subject. However, the part of the subject which has been decided in Step S3 may be excluded. In this case, it is possible to further reduce the calculation load of the ultrasound diagnostic apparatus 1 in the part determination.

Figure 6:
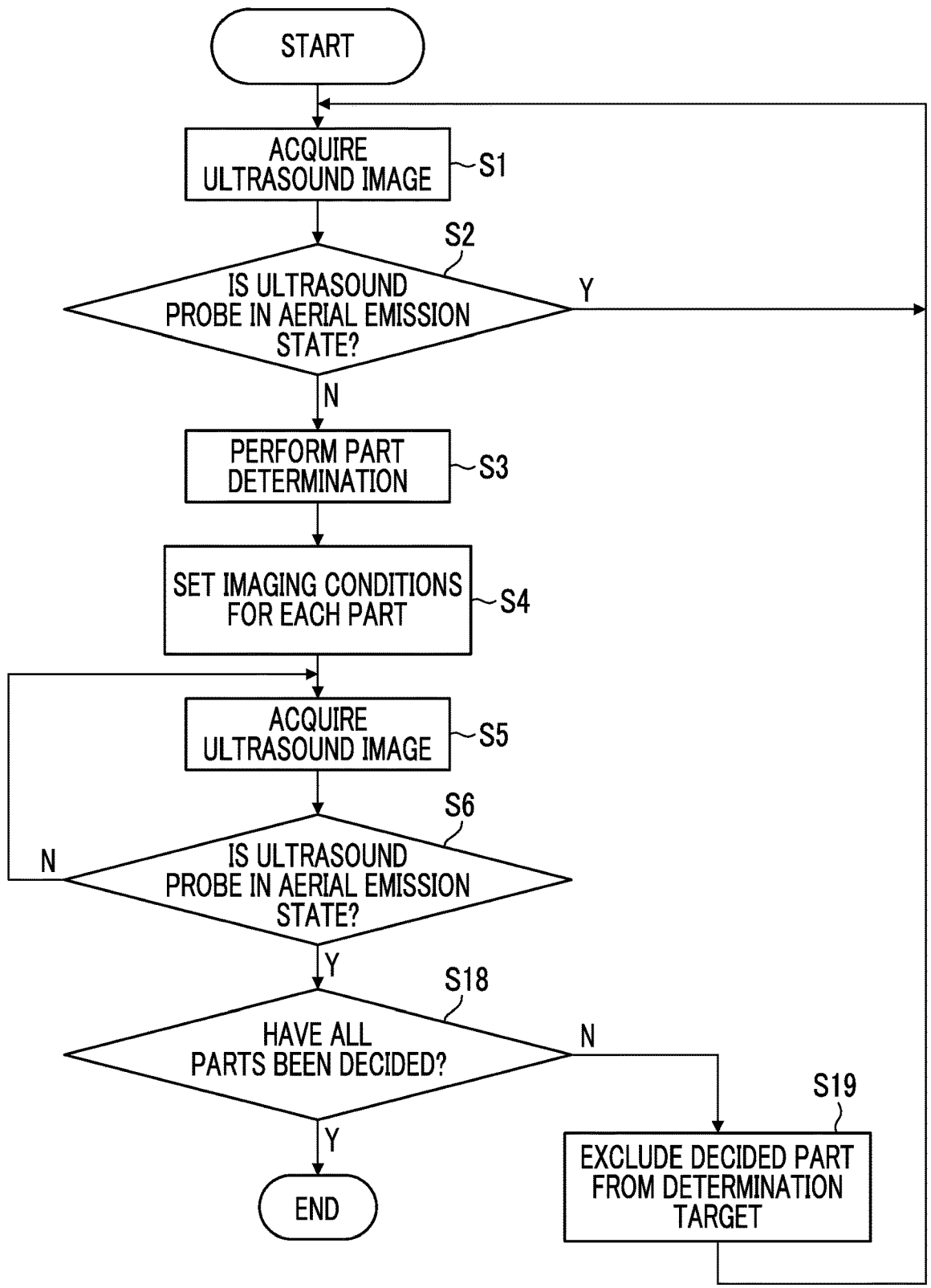
FIG. 6 is a flowchart illustrating an operation of an ultrasound diagnostic apparatus according to Embodiment 2 of the invention.

FIG. 6 illustrates the operation of an ultrasound diagnostic apparatus according to Embodiment 2. Since Steps S1 to S6 in a flowchart illustrated in FIG. 6 are the same as Steps S1 to S6 in the flowchart illustrated in FIG. 4, the detailed description thereof will not be repeated.

In a case in which the probe state detection unit 13 determines that the ultrasound probe 2 is in the aerial emission state in Step S6, the process proceeds to Step S18. In Step S18, the apparatus control unit 14 determines whether all of a plurality of parts of the subject have been decided. In a case in which it is determined in Step S18 that all of the plurality of parts of the subject have not been decided, the process proceeds to Step S19.

In Step S19, the part narrowing-down unit 11 excludes the part that has been decided in the part determination of Step S3, that is, the decided part from the determination target in Step S3 to be performed for the next time. In a case in which the process in Step S19 is completed, the process returns to Step S1. Then, in a case in which it is determined in Step S2 that the ultrasound probe 2 is not in the aerial emission state, the part determination is performed in Step S3. At that time, since the parts other than the part which has been excluded in Step S19 among the plurality of parts of the subject are the determination targets, the number of part candidates to be determined for the imaging part can be further reduced as compared with that in the part determination of Step S3 performed for the first time.

Steps S1 to S19 are repeated in this way to reduce the number of determination targets. As a result, in a case in which it is determined in Step S18 that all of the plurality of parts of the subject have been decided, the operation of the ultrasound diagnostic apparatus ends.

As such, Steps S1 to S19 are repeated to reduce the number of determination targets. Therefore, it is possible to further reduce the calculation load of the ultrasound diagnostic apparatus in the part determination of Step S3 whenever Step S19 is performed and to reduce the time required to determine the imaging part.

Embodiment 3

In a part determination operation in the flowchart of FIG. 5, the threshold value determination of Step S14 is performed for only the parts which are the determination targets narrowed down in Step S11 among the plurality of parts of the subject, but the threshold value determination can be performed for the parts which are not narrowed down in Step S11.

Figure 7:
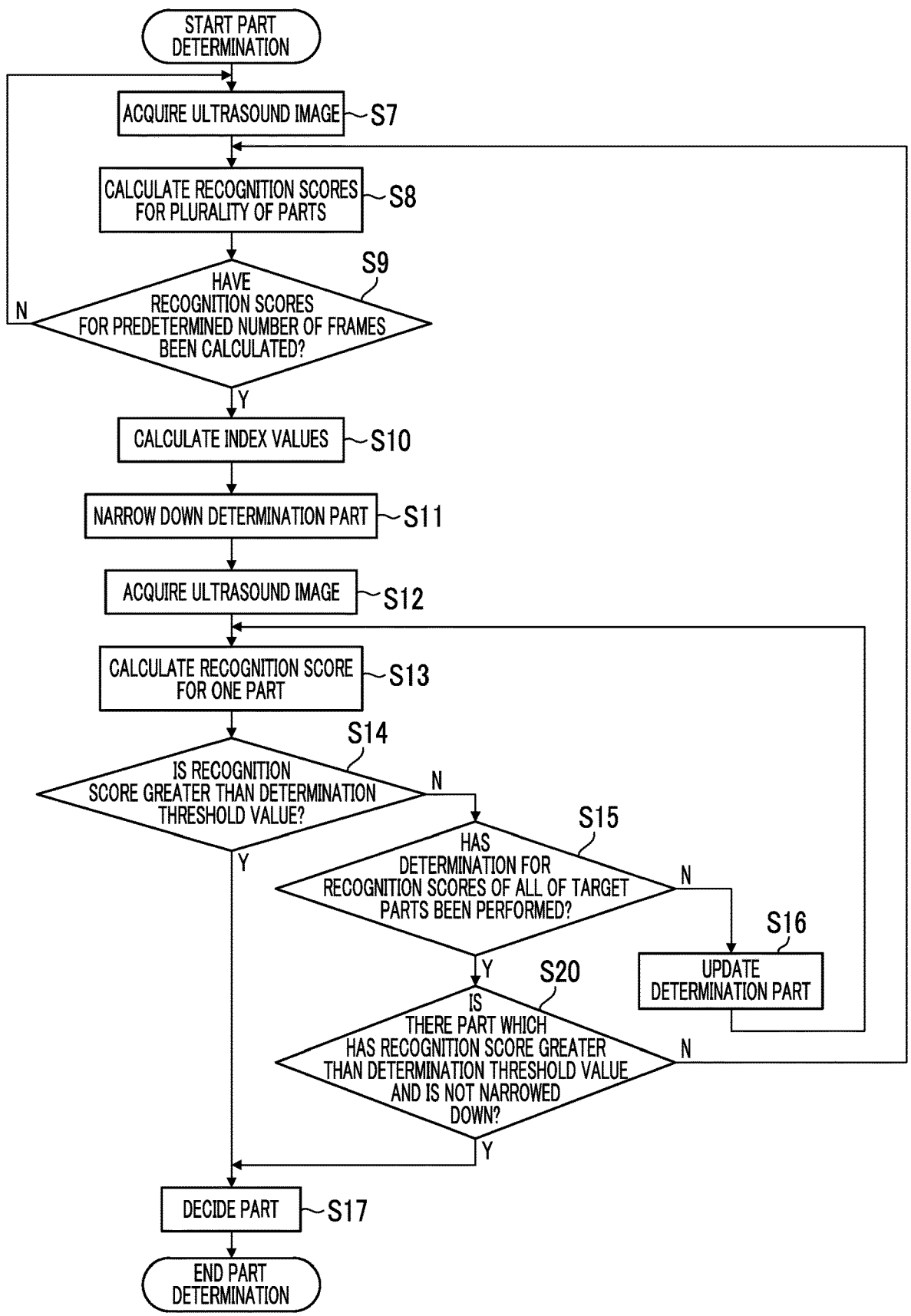
FIG. 7 is a flowchart illustrating a part determination operation of an ultrasound diagnostic apparatus according to Embodiment 3 of the invention.

FIG. 7 is a flowchart illustrating a part determination operation of an ultrasound diagnostic apparatus according to Embodiment 3. Since the flowchart of FIG. 7 is the same as the flowchart of FIG. 5 except that Step S20 is added to the flowchart of FIG. 5, the detailed description of Steps S7 to S17 is omitted.

In the flowchart of FIG. 7, in a case in which the recognition scores of the plurality of parts of the subject are calculated for a predetermined number of frames of ultrasound images in Steps S7 to S9, the index values of the plurality of parts of the subject are calculated in Step S10. In a case in which the target parts which are the determination targets for the imaging part are narrowed down on the basis of these index values in Step S11, a new ultrasound image is acquired in Step S12. In Steps S13 to S16 following Step S12, the threshold value determination is sequentially performed for the target parts of the subject narrowed down in Step S11. As a result, in a case in which it is determined in Step S15 that the threshold value determination for the recognition scores of all of the target parts narrowed down in Step S11 has been performed, the process proceeds to Step S20.

In Step S20, it is determined whether there is a part having a recognition score greater than the determination threshold value for the parts which are not narrowed down in Step S11, that is, the parts excluding the target parts that are narrowed down in Step S11 among the plurality of parts of the subject. The process performed in Step S20 will be described in detail below with reference to FIG. 8. In a case in which it is determined in Step S20 that there is no part having a recognition score greater than the determination threshold value among all of the parts which are not narrowed down in Step S11, it is determined that it is difficult to decide the part included in the ultrasound image acquired in Step S12 to be any of the plurality of parts of the subject, and the process returns to Step S8.

Meanwhile, in a case in which it is determined in Step S20 that there is a part having a recognition score greater than the determination threshold value among all of the parts which are not narrowed down in Step S11, the process proceeds to Step S17, the imaging part whose image is currently captured is decided to be a part having a recognition score greater than the determination threshold value, and the part determination operation ends.

Figure 8:
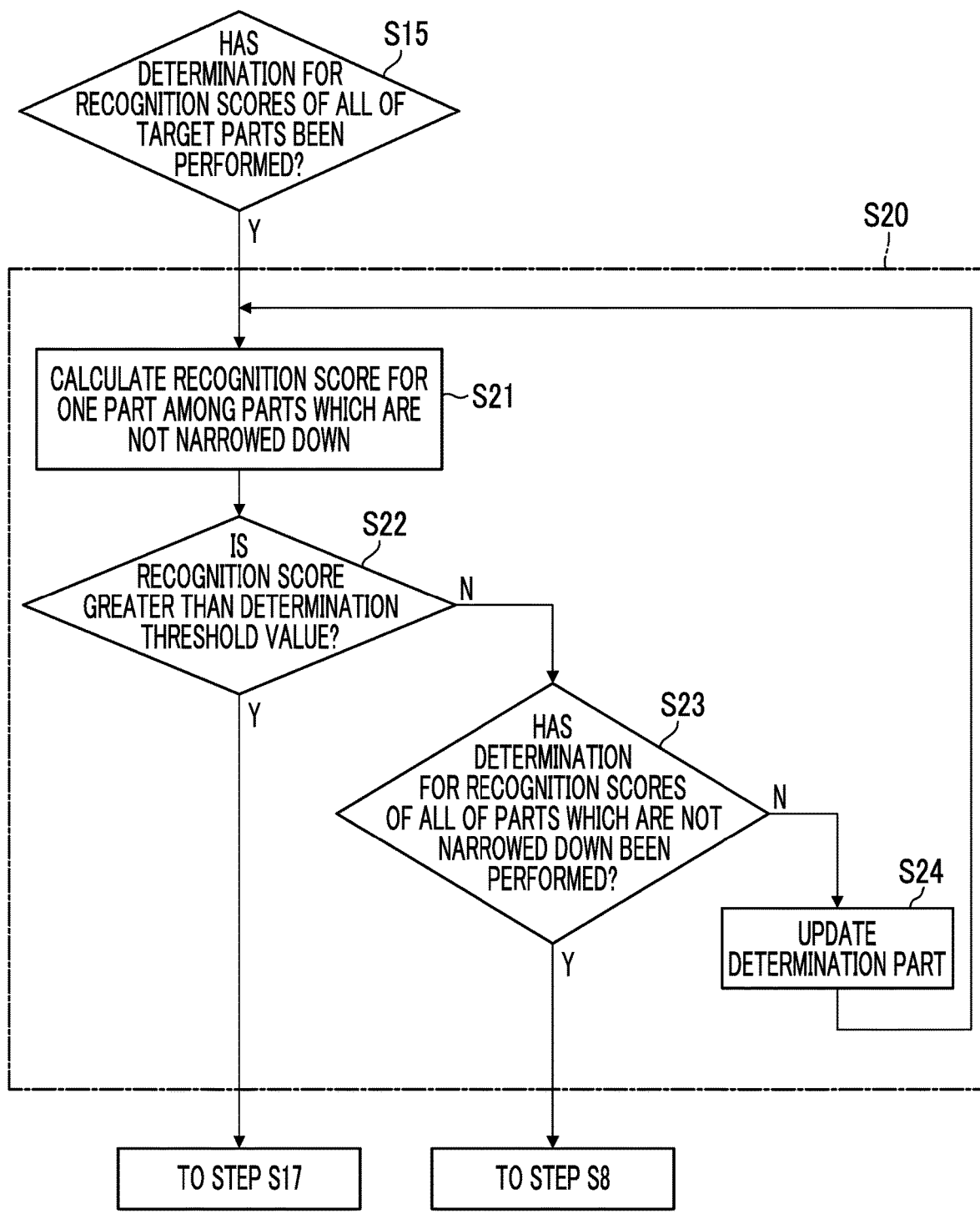
FIG. 8 is a flowchart illustrating a determination operation for parts which are not narrowed down in Embodiment 3.

Here, Step S20 of the flowchart in FIG. 7 will be described using FIG. 8. In FIG. 8, for the purpose of description, Steps S7 to S14 and Steps S16 and S17 are omitted.

In a case in which the process in Step S20 starts, first, a process in Step S21 is performed. In Step S21, the image recognition unit 9 calculates the recognition score of one part which is not narrowed down in Step S11 for the ultrasound image acquired in Step S12. In that case, the part of the subject of which the recognition score is calculated is a part ranked first in the decided order among the parts which are not narrowed down in Step S11. For example, in a case in which the plurality of parts of the subject include the heart, the lung, and the right abdominal area, the heart, the lung, and the right abdominal area are ranked in the decided order, and among these parts, only the lung is narrowed down as the target part in Step S11, the recognition score of the heart that is ranked first in the decided order among the heart and the right abdominal area which are not narrowed down in Step S11 is calculated in Step S21.

Then, in Step S22, the part determination unit 12 determines whether the recognition score calculated in Step S21 is greater than the determination threshold value. In a case in which it is determined that the recognition score calculated in Step S21 is equal to or less than the determination threshold value, the process proceeds to Step S23.

In Step S23, the apparatus control unit 14 determines whether the threshold value determination for the recognition scores of all of the parts which are not narrowed down in Step S11 has been performed in Step S22. In a case in which it is determined in Step S23 that the threshold value determination for the recognition scores of all of the parts which are not narrowed down in Step S11 has not been performed in Step S22, the process proceeds to Step S24 in order to perform the threshold value determination for the recognition score of the next part in the decided determination order.

In Step S24, the apparatus control unit 14 determines, as the determination part, the next part according to the decided order among the parts which are not narrowed down in Step S11. For example, in a case in which the plurality of parts of the subject include the heart, the lung, and the right abdominal area, the heart, the lung, and the right abdominal area are ranked in the decided order, and among these parts, only the lung is narrowed down as the target part in Step S11, the right abdominal area as the part that is ranked second in the decided order among the heart and the right abdominal area which are not narrowed down in Step S11 is determined as the determination part.

In a case in which the determination order is updated in Step S24, the process returns to Step S21. As such, as long as the recognition score of each of the parts which are not narrowed down in Step S11 is equal to or less than the determination threshold value, Steps S21 to S24 are repeated. As a result, in a case in which it is determined in Step S23 that the threshold value determination of all of the parts which are narrowed down in Step S11 has been performed in Step S22, the process returns to Step S8. This is the same as a case in which it is determined in Step S20 that there is no part having a recognition score greater than the determination threshold value among all of the parts which are not narrowed down in Step S11.

In a case in which it is determined in Step S22 that the recognition score of the part as the determination part among the parts narrowed down in Step S11 is greater than the determination threshold value, the process proceeds to Step S17. This is the same as a case in which it is determined in Step S20 that there is a part having a recognition score greater than the determination threshold value among all of the parts which are not narrowed down in Step S11.

As described above, with the part determination operation of Embodiment 3 illustrated in FIGS. 7 and 8, it is possible to perform the threshold value determination for the recognition scores of the parts of the subject which are not narrowed down in Step S11. Therefore, even in a case in which the part corresponding to the imaging part among the plurality of parts of the subject is excluded from the target part due to the accuracy of the index values calculated in Step S10, the part determination unit 12 can perform the threshold value determination for each part without exception, and it is possible to improve the accuracy of the part determination.

Embodiment 4

In the part determination operation according to Embodiments 1 and 3 illustrated in FIGS. 5 and 7, in the threshold value determination of Step S14, the recognition score of one part of the subject which has been calculated for the ultrasound image newly acquired in Step S12 by the image recognition unit 9 is used. However, recognition scores for part determination which have been calculated on the basis of the recognition scores calculated for a plurality of ultrasound images may be used for the threshold value determination.

Figure 9:
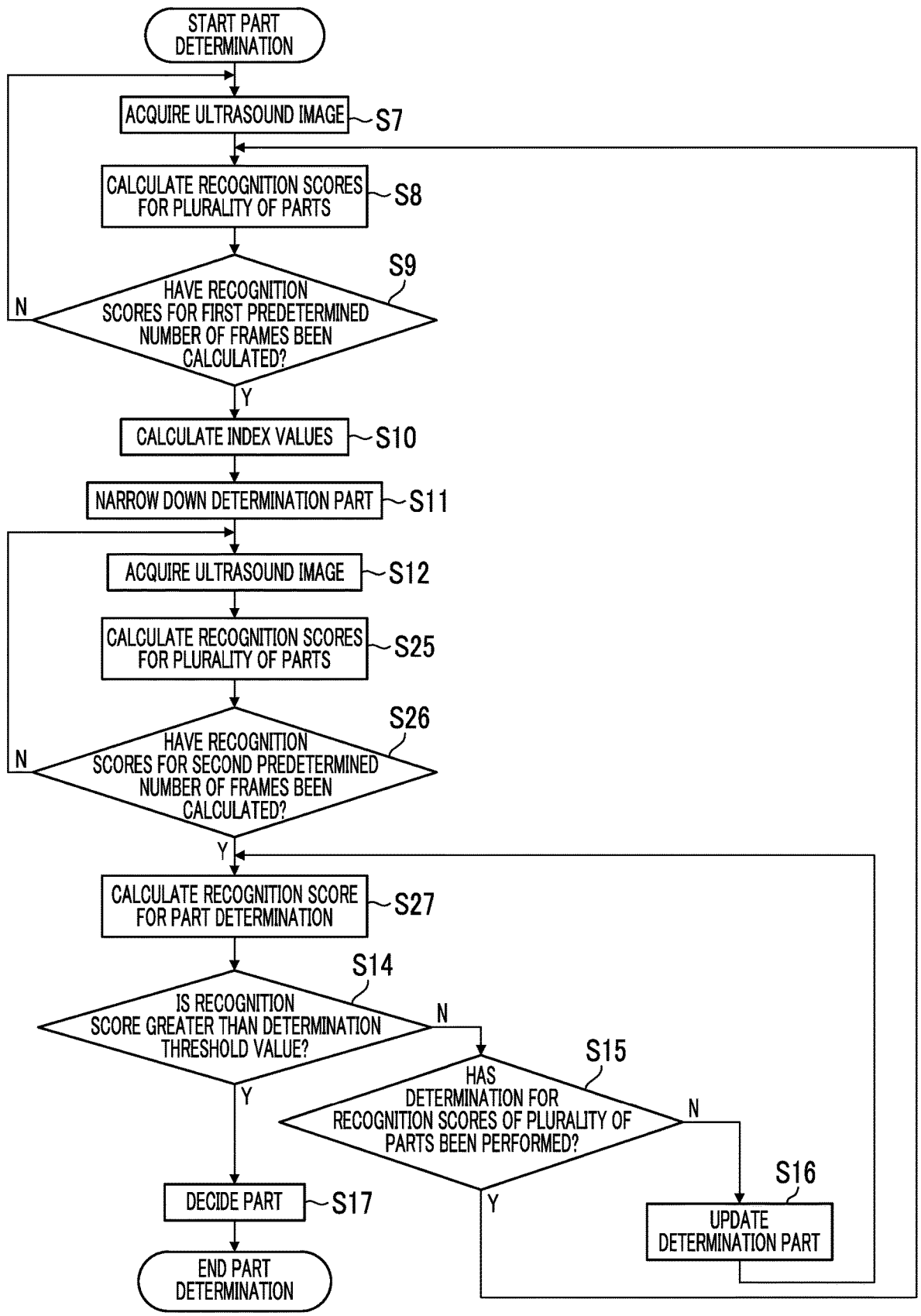
FIG. 9 is a flowchart illustrating a part determination operation of an ultrasound diagnostic apparatus according to Embodiment 4 of the invention.

FIG. 9 is a flowchart illustrating a part determination operation of an ultrasound diagnostic apparatus according to Embodiment 4. The flowchart illustrated in FIG. 9 is the same as the flowchart according to Embodiment 1 illustrated in FIG. 5 except for Steps S20 to S22.

In the flowchart illustrated in FIG. 9, in a case in which the part determination operation starts, first, Steps S7 to S9 are repeated until the recognition scores of a plurality of parts of the subject are calculated for a predetermined number of frames of ultrasound images. Here, the predetermined number of frames is referred to as a first predetermined number of frames for the purpose of description. In a case in which it is determined in Step S9 that the recognition scores of the plurality of parts of the subject are calculated for the first predetermined number of frames of ultrasound images, the process proceeds to Step S10. In a case in which the index values of the plurality of parts of the subject are calculated from the recognition scores of the plurality of parts of the subject calculated for the first predetermined number of frames of ultrasound images in Step S10, target parts which are the targets for the part determination are narrowed down from among the plurality of parts of the subject in Step S11.

Then, an ultrasound image is newly acquired in Step S12 and the process proceeds to Step S20. Step S20 is the same as Step S8 in the flowchart illustrated in FIG. 5. In a case in which the recognition scores of the plurality of parts of the subject are calculated for the latest ultrasound image in Step S25, the process proceeds to Step S26.

In Step S26, the apparatus control unit 14 determines whether recognition scores have been calculated for a second predetermined number of frames of ultrasound images acquired in Step S12. This is to obtain the number of recognition scores necessary to calculate the recognition scores for part determination. Therefore, in a case in which it is determined in Step S26 that the recognition scores have not been calculated for the second predetermined number of frames of ultrasound images, the process returns to Step S12, and an ultrasound image is newly acquired. Then, in Step S25, the recognition scores of the plurality of parts of the subject are newly calculated.

Here, the first predetermined number of frames in Step S9 and the second predetermined number of frames in Step S26 may be equal to or different from each other. For the purpose of description, it is assumed that the first predetermined number of frames and the second predetermined number of frames are different from each other.

In a case in which it is determined in Step S26 that the recognition scores have been calculated for the second predetermined number of frames of ultrasound images, the process proceeds to Step S27. In Step S27, the image recognition unit 9 averages the recognition scores of the determination part which have been calculated in Step S25 for the second predetermined number of frames of ultrasound images. In that case, the part of which the recognition score is calculated is a determination part ranked first in the decided determination order among the target parts narrowed down in Step S11. As such, the image recognition unit 9 calculates the mean value of the recognition scores of the determination part as the recognition score for determining the imaging part. In this case, it is preferable that a plurality of ultrasound images used to recognize the determination part are continuous in time series.

Then, in Step S14, the apparatus control unit 14 determines whether the recognition score for determination calculated in Step S27 is greater than the determination threshold value. In a case in which it is determined in Step S14 that the recognition score for determination is equal to or less than the determination threshold value, it is difficult to decide the determination part with respect to the imaging part, and the process proceeds to Step S15. In a case in which it is determined in Step S15 that the threshold value determination for the recognition scores of all of the target parts narrowed down in Step S11 has not been performed, the determination part is updated in Step S16, and the process returns to Step S27.

In a case in which the process returns to Step S27, the recognition score for determination is calculated for the part that is ranked second in the decided determination order among the target parts narrowed down in Step S11. As such, as long as the recognition score for determination is equal to or less than the determination threshold value in Step S14, Steps S27 to S16 are repeated. In a case in which it is determined in Step S14 that the recognition score for determination is greater than the determination threshold value, the process proceeds to Step S17, and the imaging part is decided. Then, the part determination operation illustrated in the flowchart of FIG. 9 ends.

As such, since the recognition score for part determination is calculated from the recognition scores calculated for a plurality of ultrasound images, it is possible to improve the accuracy of determining the imaging part. For example, even in a case in which a part of the subject included in some of the ultrasound images acquired in Step S12 is not sufficiently clear as the image recognition target, the accuracy of deciding the imaging part is improved.

In the above description, in a case in which the recognition score for determining the imaging part is calculated in Step S27, the recognition scores for the second predetermined number of frames of ultrasound images acquired in Step S12 are used. However, the recognition score for determining the imaging part may be calculated in Step S27 on the basis of both the recognition scores calculated in Step S25 and the recognition scores for the first predetermined number of frames of ultrasound images. That is, the second predetermined number of frames may be the sum of the first predetermined number of frames and the number of frames of ultrasound images acquired in Step S12.

At that time, in a case in which the second predetermined number of frames is equal to or less than the first predetermined number of frames, that is, in a case in which the number of recognition scores of a plurality of parts of the subject required to calculate the recognition score for determining the imaging part in Step S27 is equal to or less than the number of recognition scores required to calculate the index values in Step S10, Step S12, Step S25, and Step S26 can be omitted. Therefore, it is possible to further reduce the time required to determine the imaging part.

Embodiment 5

In the part determination operations according to Embodiments 1, 3, and 4 illustrated in FIGS. 5, 7, and 9, the determination target parts for the imaging part are narrowed down from among a plurality of parts of the subject on the basis of the index values of the plurality of parts of the subject. However, at that time, the determination order in which the threshold value determination is performed can be decided.

Figure 10:
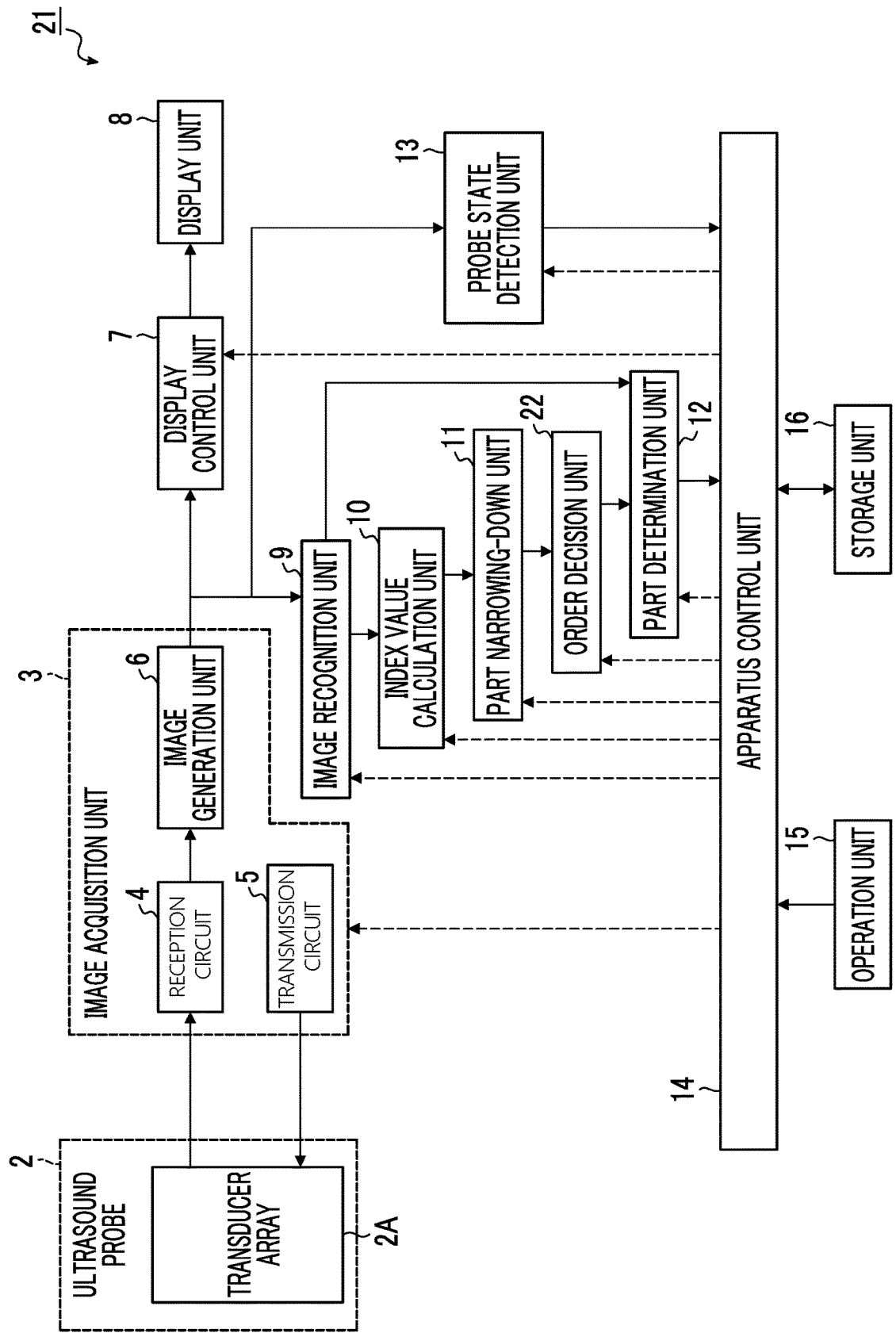
FIG. 10 is a block diagram illustrating the configuration of an ultrasound diagnostic apparatus according to Embodiment 5 of the invention.

FIG. 10 illustrates the configuration of an ultrasound diagnostic apparatus 21 according to Embodiment 5. The ultrasound diagnostic apparatus 21 according to Embodiment 5 is the same as the ultrasound diagnostic apparatus 1 according to Embodiment 1 illustrated in FIG. 1 except that the ultrasound diagnostic apparatus 21 includes an order decision unit 22. Therefore, components other than the order decision unit 22 are denoted by the same reference numerals and the detailed description thereof will not be repeated.

In the ultrasound diagnostic apparatus 21 according to Embodiment 5, the order decision unit 22 is connected to the part narrowing-down unit 11, and the order decision unit 22 is connected to the part determination unit 12. In addition, the order decision unit 22 is connected to the apparatus control unit 14.

The order decision unit 22 decides a determination order in which part determination is performed for the plurality of parts of the subject, on the basis of the index values of the plurality of parts of the subject calculated by the index value calculation unit 10. In that case, the order decision unit 22 decides the determination order such that the part with a larger index value is ranked higher.

Figure 11:
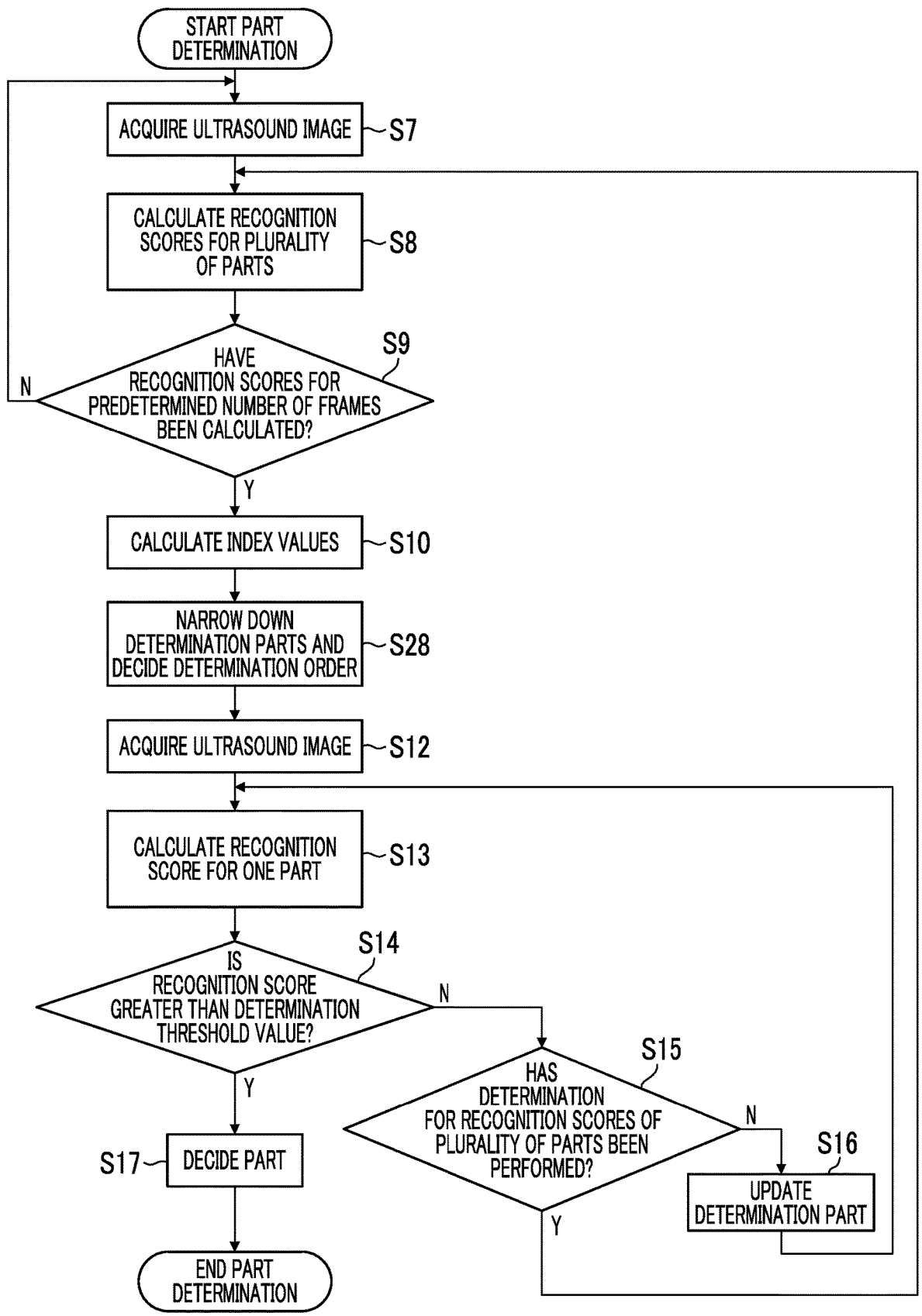
FIG. 11 is a flowchart illustrating a part determination operation of the ultrasound diagnostic apparatus according to Embodiment 5 of the invention.

FIG. 11 is a flowchart illustrating a part determination operation of the ultrasound diagnostic apparatus 21 according to Embodiment 5. The flowchart illustrated in FIG. 11 is the same as the flowchart illustrated in FIG. 5 except that Step S11 in the flowchart according to Embodiment 1 illustrated in FIG. 5 is replaced with Step S28. Therefore, the detailed description of the same steps as those in the flowchart of FIG. 5 will not be repeated.

In a case in which the part determination operation of the ultrasound diagnostic apparatus 21 according to Embodiment 5 starts, the recognition scores of a plurality of parts of the subject are calculated for a predetermined number of frames of ultrasound images in Steps S7 to S9. Then, in Step S10, index values are calculated on the basis of the recognition scores.

Then, in Step S28, first, the part narrowing-down unit 11 narrows down the target parts to be determined with respect to the imaging part whose image is currently captured, on the basis of the index values of the plurality of parts of the subject calculated in Step S10. Then, the order decision unit 22 decides the determination order of a plurality of parts narrowed down by the part narrowing-down unit 11 such that the part with a larger index value is ranked higher.

Then, in Steps S12 and S13, an ultrasound image is newly acquired, and only the recognition score of a part that is ranked first in the determination order among the target parts narrowed down in Step S28 is calculated. Then, in Steps S14 to S16, it is determined whether the recognition score is greater than the determination threshold value and the determination part is updated. In Step S16, the determination part is continuously updated. As a result, in a case in which it is determined in Step S15 that the threshold value determination for the recognition scores of all of the target parts narrowed down in Step S28 has been performed in Step S14, it is determined that it is difficult to decide the part included in the ultrasound image acquired in Step S12 to be any of the plurality of parts of the subject, and the process returns to Step S8. Then, the part determination operation starts again.

In a case in which it is determined in Step S14 that the recognition score of the part calculated in Step S13 is greater than the threshold value, the process proceeds to Step S17. In a case in which the part to be determined with respect to the imaging part whose image is currently captured is decided in Step S17, the part determination operation ends.

As described above, in the part determination operation according to Embodiment 5, since the target parts for the determination of the imaging part whose image is currently captured are narrowed down and the determination order of the narrowed-down target parts is decided, it is possible to perform the threshold value determination of the recognition score sequentially from the part with a high probability of being the imaging part. Therefore, it is possible to reduce the calculation load of the ultrasound diagnostic apparatus 21 in the part determination and to reduce the time required to determine the imaging part.

In Embodiment 5, the order decision unit 22 decides the determination order of the target parts of the subject which are narrowed down by the part narrowing-down unit 11. However, similarly to Embodiment 3, in a case in which the threshold value determination is performed for the parts which are not narrowed down by the part narrowing-down unit 11, the determination order of the parts which are not narrowed down by the part narrowing-down unit 11 can be decided. In this case, similarly to a case in which the determination order of the target parts is decided, the order decision unit 22 can decide the order of the parts which are not narrowed down by the part narrowing-down unit 11, on the basis of the index values of the parts. Although not illustrated, for example, the order decision unit 22 may decide the order of the parts which are not narrowed down by the part narrowing-down unit 11, immediately before the step corresponding to Step S20 in the flowchart of Embodiment 3 illustrated in FIG. 7.

In addition, in some cases, the index value calculation unit 10 may calculate the same index values among the index values of the plurality of parts of the subject. The order decision unit 22 decides the determination order such that the part with a larger index value is ranked higher. Therefore, in a case in which the same index values among the index values of the plurality of parts which are narrowed down by the part narrowing-down unit 11 are calculated, it is difficult for the order decision unit 22 to decide the determination order. In that case, the index value calculation unit 10 can calculate the index values again. Further, in that case, the index value calculation unit 10 can calculate the index values again, using the recognition scores calculated for an ultrasound image group that includes the latest ultrasound image acquired by the image acquisition unit 3 and consists of ultrasound images whose number is less than the number of the plurality of ultrasound images used in a case in which the same index values have been calculated. It is preferable that the ultrasound image group used here is continuously acquired in time series by the image acquisition unit 3.

In addition, in a case in which the index values are calculated again, the index value calculation unit 10 may calculate the index values, using the recognition scores calculated for an ultrasound image group consisting of a plurality of ultrasound images that are acquired by the image acquisition unit 3 before the latest ultrasound image in time series and are continuous in time series.

The ultrasound diagnostic apparatuses according to the embodiments of the invention have been described in detail above. However, the invention is not limited to the above-mentioned examples and various modifications and changes may be made without departing from the scope and spirit of the invention. In addition, a plurality of embodiments described above may be appropriately combined with each other.

EXPLANATION OF REFERENCES 1, 21: ultrasound diagnostic apparatus
2: ultrasound probe
2A: transducer array
3: image acquisition unit
4: receiving unit
5: transmitting unit
6: image generation unit
7: display control unit
8: display unit
9: image recognition unit
10: index value calculation unit
11: part narrowing-down unit
12: part determination unit
13: probe state detection unit
14: apparatus control unit
15: operation unit
16: storage unit
17: amplification unit
18: A/D conversion unit
19: B-mode processing unit
20: image processing unit
22: order decision unit

What is claimed is:
1. A method for controlling an ultrasound diagnostic apparatus, the method comprising:
transmitting, via a transmission circuit, an ultrasound beam from an ultrasound probe to a subject;
receiving, via a reception circuit, ultrasound echoes from the subject by the ultrasound probe to generate element data;
generating an ultrasound image on the basis of the element data;
calculating recognition scores by performing image recognition for predetermined number of ultrasound images which are continuously acquired in time series and include a latest ultrasound image acquired, where each of recognition scores is a similarity between each of a plurality of organs of the subject and an imaging organ in the ultrasound image;

calculating mean values or medians of the recognition scores of the plurality of organs for the plurality of ultrasound images as index values;

narrowing down target organs which are candidates to be determined for the imaging organ, from the plurality of organs on the basis of the index values for the plurality of organs;

determining the imaging organ of the subject among the target organs which are narrowed down on the basis of the calculated recognition scores for the target organs which are narrowed down;

setting imaging conditions suitable for the imaging organ;

acquiring a new ultrasound image by using the imaging conditions suitable for the imaging organ; and displaying the new ultrasound image on a display.

2. The method for controlling an ultrasound diagnostic apparatus according to claim 1, the method further comprising:

detecting a change in the imaging organ caused by movement of the ultrasound probe and starting to calculate the index value after detecting the change in the imaging organ.

3. The method for controlling an ultrasound diagnostic apparatus according to claim 1, the method further comprising:

having a narrowing-down threshold value for the index value, and narrowing down the plurality of organs of the subject having the index value greater than the narrowing-down threshold value, as the target organs.

4. The method for controlling an ultrasound diagnostic apparatus according to claim 1, the method further comprising:

deciding a determination order in which determination is performed for the plurality of organs, on the basis of the index values and decide the determination order such that the organ with a larger index value is ranked higher.

5. The method for controlling an ultrasound diagnostic apparatus according to claim 1, the method further comprising:

determining the imaging organ on the basis of the calculated recognition scores for the organs excluding the target organs from the plurality of organs of the subject in a case in which the imaging organ is not decided to any target organs which are narrowed down.

6. A method for controlling an ultrasound diagnostic apparatus, the method comprising:

transmitting, via a transmission circuit, an ultrasound beam from an ultrasound probe to a subject;

receiving, via a reception circuit, ultrasound echoes from the subject by the ultrasound probe to generate element data;

generating an ultrasound image on the basis of the element data;

calculating recognition scores by performing image recognition for predetermined number of ultrasound images which are continuously acquired in time series and include a latest ultrasound image acquired, where each of recognition scores is a similarity between each of a plurality of organs of the subject and an imaging organ in the ultrasound image;

calculating maximum values or minimum values of the recognition scores of the plurality of organs for plurality of ultrasound images as index values;

narrowing down target organs which are candidates to be determined for the imaging organ, from the plurality of organs on the basis of the index values for the plurality of organs;

determining the imaging organ of the subject among the target organs which are narrowed down on the basis of the calculated recognition scores for the target organs which are narrowed down;

setting imaging conditions suitable for the imaging organ;

acquiring a new ultrasound image by using the imaging conditions suitable for the imaging organ; and displaying the new ultrasound image on a display.

7. The method for controlling an ultrasound diagnostic apparatus according to claim 6, the method further comprising:

detecting a change in the imaging organ caused by movement of the ultrasound probe and starting to calculate the index value after detecting the change in the imaging organ.

8. The method for controlling an ultrasound diagnostic apparatus according to claim 6, the method further comprising:

having a narrowing-down threshold value for the index value, and narrowing down the plurality of organs of the subject having the index value greater than the narrowing-down threshold value, as the target organs.

9. The method for controlling an ultrasound diagnostic apparatus according to claim 6, the method further comprising:

deciding a determination order in which determination is performed for the plurality of organs, on the basis of the index values and decide the determination order such that the organ with a larger index value is ranked higher.

10. The method for controlling an ultrasound diagnostic apparatus according to claim 6, the method further comprising:

determining the imaging organ on the basis of the calculated recognition scores for the organs excluding the target organs from the plurality of organs of the subject in a case in which the imaging organ is not decided to any target organs which are narrowed down.

11. A method for controlling an ultrasound diagnostic apparatus, the method comprising:

transmitting, via a transmission circuit, an ultrasound beam from an ultrasound probe to a subject;

receiving, via a reception circuit, ultrasound echoes from the subject by the ultrasound probe to generate element data;

generating an ultrasound image on the basis of the element data;

calculating recognition scores by performing image recognition for predetermined number of ultrasound images which are continuously acquired in time series and include a latest ultrasound image acquired, where each of recognition scores is a similarity between each of a plurality of organs of the subject and an imaging organ in the ultrasound image;

calculating weighted mean values of the recognition scores of the plurality of organs as index values by giving a larger weight to an ultrasound image more recently acquired among the plurality of ultrasound images;

narrowing down target organs which are candidates to be determined for the imaging organ, from the plurality of organs on the basis of the index values for the plurality of organs;
determining the imaging organ of the subject among the target organs which are narrowed down on the basis of the calculated recognition scores for the target organs which are narrowed down;
setting imaging conditions suitable for the imaging organ;
acquiring a new ultrasound image by using the imaging conditions suitable for the imaging organ; and
displaying the new ultrasound image on a display.

12. The method for controlling an ultrasound diagnostic apparatus according to claim 11, the method further comprising:
detecting a change in the imaging organ caused by movement of the ultrasound probe and starting to calculate the index value after detecting the change in the imaging organ.

13. The method for controlling an ultrasound diagnostic apparatus according to claim 11, the method further comprising:
having a narrowing-down threshold value for the index value, and narrowing down the plurality of organs of the subject having the index value greater than the narrowing-down threshold value, as the target organs.

14. The method for controlling an ultrasound diagnostic apparatus according to claim 11, the method further comprising:
deciding a determination order in which determination is performed for the plurality of organs, on the basis of the index values and decide the determination order such that the organ with a larger index value is ranked higher.

15. The method for controlling an ultrasound diagnostic apparatus according to claim 11, the method further comprising:
determining the imaging organ on the basis of the calculated recognition scores for the organs excluding the target organs from the plurality of organs of the subject in a case in which the imaging organ is not decided to any target organs which are narrowed down.

16. A method for controlling an ultrasound diagnostic apparatus, the method comprising:
transmitting, via a transmission circuit, an ultrasound beam from an ultrasound probe to a subject;
receiving, via a reception circuit, ultrasound echoes from the subject by the ultrasound probe to generate element data;
generating an ultrasound image on the basis of the element data;
calculating recognition scores by performing image recognition for predetermined number of ultrasound images which are continuously acquired in time series and include a latest ultrasound image acquired, where each of recognition scores is a similarity between each of a plurality of organs of the subject and an imaging organ in the ultrasound image;
giving ranking scores to the plurality of organs for each of the plurality of ultrasound images such that the organ with a higher recognition score has a higher ranking score;
calculating sums of the ranking scores of the plurality of organs for the plurality of ultrasound images as index values;
narrowing down target organs which are candidates to be determined for the imaging organ, from the plurality of organs on the basis of the index values for the plurality of organs;
determining the imaging organ of the subject among the target organs which are narrowed down on the basis of the calculated recognition scores for the target organs which are narrowed down;
setting imaging conditions suitable for the imaging organ;
acquiring a new ultrasound image by using the imaging conditions suitable for the imaging organ; and
displaying the new ultrasound image on a display.

17. The method for controlling an ultrasound diagnostic apparatus according to claim 16, the method further comprising:
detecting a change in the imaging organ caused by movement of the ultrasound probe and starting to calculate the index value after detecting the change in the imaging organ.

18. The method for controlling an ultrasound diagnostic apparatus according to claim 16, the method further comprising:
having a narrowing-down threshold value for the index value, and narrowing down the plurality of organs of the subject having the index value greater than the narrowing-down threshold value, as the target organs.

19. The method for controlling an ultrasound diagnostic apparatus according to claim 16, the method further comprising:
deciding a determination order in which determination is performed for the plurality of organs, on the basis of the index values and decide the determination order such that the organ with a larger index value is ranked higher.

20. The method for controlling an ultrasound diagnostic apparatus according to claim 16, the method further comprising:
determining the imaging organ on the basis of the calculated recognition scores for the organs excluding the target organs from the plurality of organs of the subject in a case in which the imaging organ is not decided to any target organs which are narrowed down.

21. A method for controlling an ultrasound diagnostic apparatus, the method comprising:
transmitting, via a transmission circuit, an ultrasound beam from an ultrasound probe to a subject;
receiving, via a reception circuit, ultrasound echoes from the subject by the ultrasound probe to generate element data;
generating an ultrasound image on the basis of the element data;
calculating recognition scores by performing image recognition for predetermined number of ultrasound images which are continuously acquired in time series and include a latest ultrasound image acquired, where each of recognition scores is a similarity between each of a plurality of organs of the subject and an imaging organ in the ultrasound image;
acquiring a number of recognition scores greater than a predetermined threshold value among the recognition scores of the plurality of organs calculated for the plurality of ultrasound images as index values;
narrowing down target organs which are candidates to be determined for the imaging organ, from the plurality of organs on the basis of the index values for the plurality of organs;

determining the imaging organ of the subject among the target organs which are narrowed down on the basis of the calculated recognition scores for the target organs which are narrowed down;

setting imaging conditions suitable for the imaging organ;

acquiring a new ultrasound image by using the imaging conditions suitable for the imaging organ; and displaying the new ultrasound image on a display.

22. The method for controlling an ultrasound diagnostic apparatus according to claim 21, the method further comprising:

detecting a change in the imaging organ caused by movement of the ultrasound probe and starting to calculate the index value after detecting the change in the imaging organ.

23. The method for controlling an ultrasound diagnostic apparatus according to claim 21, the method further comprising:

having a narrowing-down threshold value for the index value, and narrowing down the plurality of organs of the subject having the index value greater than the narrowing-down threshold value, as the target organs.

24. The method for controlling an ultrasound diagnostic apparatus according to claim 21, the method further comprising:

deciding a determination order in which determination is performed for the plurality of organs, on the basis of the index values and decide the determination order such that the organ with a larger index value is ranked higher.

25. The method for controlling an ultrasound diagnostic apparatus according to claim 21, the method further comprising:

determining the imaging organ on the basis of the calculated recognition scores for the organs excluding the target organs from the plurality of organs of the subject in a case in which the imaging organ is not decided to any target organs which are narrowed down.

* * * * *